(12) United States Patent
Hartwig et al.

US009598340B2

(10) Patent No.: US 9,598,340 B2
(45) Date of Patent: Mar. 21, 2017

(54) METAL-CATALYZED COUPLING OF ARYL AND VINYL HALIDES WITH ALPHA, ALPHA-DIFLUOROCARBONYL COMPOUNDS

(71) Applicant: THE REGENTS OF THE UNIVERSITY OF CALIFORNIA, Oakland, CA (US)

(72) Inventors: John F. Hartwig, Berkeley, CA (US); Shaozhong Ge, Albany, CA (US); Wojciech Chaładaj, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/782,402

(22) PCT Filed: Apr. 7, 2014

(86) PCT No.: PCT/US2014/033227
§ 371 (c)(1),
(2) Date: Oct. 5, 2015

(87) PCT Pub. No.: WO2014/165861
PCT Pub. Date: Oct. 9, 2014

(65) Prior Publication Data
US 2016/0052854 A1    Feb. 25, 2016

Related U.S. Application Data

(60) Provisional application No. 61/809,262, filed on Apr. 5, 2013.

(51) Int. Cl.
| | |
|---|---|
| C07F 15/00 | (2006.01) |
| C07C 45/86 | (2006.01) |
| C07C 49/80 | (2006.01) |
| B01J 23/44 | (2006.01) |
| C07C 45/68 | (2006.01) |
| B01J 31/24 | (2006.01) |
| C07B 39/00 | (2006.01) |
| C07C 17/361 | (2006.01) |
| C07C 41/18 | (2006.01) |
| C07C 45/00 | (2006.01) |
| C07C 67/297 | (2006.01) |
| C07C 67/343 | (2006.01) |
| C07C 67/42 | (2006.01) |
| C07C 69/612 | (2006.01) |
| C07C 69/76 | (2006.01) |
| C07C 201/12 | (2006.01) |
| C07C 205/45 | (2006.01) |
| C07C 221/00 | (2006.01) |
| C07C 225/22 | (2006.01) |
| C07C 231/12 | (2006.01) |
| C07C 269/06 | (2006.01) |
| C07C 319/20 | (2006.01) |
| C07C 323/22 | (2006.01) |
| C07D 213/50 | (2006.01) |
| C07D 213/56 | (2006.01) |
| C07D 215/12 | (2006.01) |
| C07D 215/14 | (2006.01) |

(Continued)

(52) U.S. Cl.
CPC ............. *C07C 45/68* (2013.01); *B01J 23/44* (2013.01); *B01J 31/2404* (2013.01); *C07B 39/00* (2013.01); *C07C 17/361* (2013.01); *C07C 41/18* (2013.01); *C07C 45/004* (2013.01); *C07C 45/86* (2013.01); *C07C 49/80* (2013.01); *C07C 67/297* (2013.01); *C07C 67/343* (2013.01); *C07C 67/42* (2013.01); *C07C 69/612* (2013.01); *C07C 69/76* (2013.01); *C07C 201/12* (2013.01); *C07C 205/45* (2013.01); *C07C 221/00* (2013.01); *C07C 225/22* (2013.01); *C07C 231/12* (2013.01); *C07C 269/06* (2013.01); *C07C 319/20* (2013.01); *C07C 323/22* (2013.01); *C07D 213/50* (2013.01); *C07D 213/56* (2013.01); *C07D 215/12* (2013.01); *C07D 215/14* (2013.01); *C07D 217/18* (2013.01); *C07D 295/104* (2013.01); *C07D 317/16* (2013.01); *C07D 317/26* (2013.01); *C07D 317/54* (2013.01); *C07D 333/24* (2013.01); *C07F 7/083* (2013.01); *C07F 7/0818* (2013.01); *C07F 15/006* (2013.01); *B01J 2531/824* (2013.01)

(58) Field of Classification Search
CPC ...... C07F 15/006; B01J 23/44; B01J 31/2404; C07C 45/68; C07C 49/80; C07C 49/84
USPC .............. 568/56, 315, 316, 322, 331, 649; 570/127; 556/22; 560/51, 109; 544/69, 544/165, 176; 546/174, 146, 446, 445
See application file for complete search history.

(56) References Cited

FOREIGN PATENT DOCUMENTS

WO    WO 2014/165861 A1    10/2014

OTHER PUBLICATIONS

Zhang et al., Eur. J. Org. Chem., 2014(6), pp. 1327-1332 (2014).*
Albert, J; Granell, J.; Zafrilla, J.; Font-Bardia, M.; Solans, X. J. Organomet. Chem. 2005, 690 422.
Aráoz, et al., Biochemistry, 2000, 39:15971.

(Continued)

*Primary Examiner* — Porfirio Nazario Gonzalez
(74) *Attorney, Agent, or Firm* — Morgan, Lewis & Bockius LLP; Jeffry S. Mann

(57) ABSTRACT

The coupling of aryl, heteroaryl, and vinyl halides with α,α-difluoroketones or silyl ethers or siylenol ethers of α,α-difluoroketones and α,α-difluoroamides and esters are described. Further derivatization of the coupling products (such as ketone cleavage and Baeyer-Villiger oxidation) is also described.

23 Claims, 2 Drawing Sheets

(51) Int. Cl.

| | |
|---|---|
| *C07D 217/18* | (2006.01) |
| *C07D 295/104* | (2006.01) |
| *C07D 317/16* | (2006.01) |
| *C07D 317/26* | (2006.01) |
| *C07D 317/54* | (2006.01) |
| *C07D 333/24* | (2006.01) |
| *C07F 7/08* | (2006.01) |

(56) References Cited

OTHER PUBLICATIONS

Dolbier, et al., J. Org. Chem., 2008, 73:2469.
Feng, et al., Angew. Chem., Int. Ed., 2014, 53:1669.
Fier, et al., J Am. Chem. Soc., 2012, 134:5524.
Fujikawa, et al., Org. Lett., 2011, 13:5560.
Fujikawa, et al., Synthesis, 2012, 44:3015.
Fujiwara, et al., J. Am. Chem. Soc., 2012, 134:1494.
Guo, C.; Wang, R.-W.; Qing, F.-L. J. Fluor. Chem., 2012, 143, 135-142.
Guo, Y.; Shreeve, J. M. Chem. Commun. 2007, 3583-3585.
Hope, H. R., J. Lipid Res., 2000, 41:1604.
Kobayashi,S.; Tanaka, H.; Amii, H.; Uneyama, K. Tetrahedron 2003, 59 1547-1552.
Markovskij, et al., Synthesis, 1973, 787.
Middleton, W. J., J. Org. Chem., 1975, 40:574.
Prakash, et al., Angew. Chem., Int. Ed., 2012, 51:12090.
Purser, et al., Chem. Soc. Rev., 2008, 37:320.
Wang, et al., Chem. Rev., 2014, 114:2432.
Zemtsov, et al., J. Org. Chem., 2013, 79:818.

\* cited by examiner

METAL-CATALYZED COUPLING OF ARYL AND VINYL HALIDES WITH ALPHA, ALPHA-DIFLUOROCARBONYL COMPOUNDS

CROSS-REFERENCE TO RELATED APPLICATIONS

This application claims under 35 USC 119(e) the benefit of U.S. Provisional Application No. 61/809,262, filed Apr. 5, 2013, which is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with Government support under Grant No. GM-58108 awarded by the National Institutes of Health. The Government has certain rights in the invention.

BACKGROUND OF THE INVENTION

Selectively fluorinated organic compounds present a range of interesting and unique properties, particularly attractive to pharmaceutical, material and agricultural sciences. For this reason, development of the synthetic methods for introduction of fluorinated groups into organic molecules has recently become a subject of remarkably growing interest. However, efficient, mild and selective protocols, especially employing transition metal complexes as catalysts, are still rare. For instance, catalytic method for arylation of α,α-difluoroketones requires high palladium and ligand loading to give product, which is moreover hardly separable from the byproduct formed in considerable amounts (Guo, C.; Wang, R.-W.; Qing, F.-L. *J. Fluor. Chem.*, 2012, 143, 135-142). Alternatively, corresponding silyl enol ether can be applied, but addition of toxic tributyltin fluoride is necessary to facilitate transmetallation (Guo, Y.; Shreeve, J. M. *Chem. Commun.* 2007, 3583-3585).

The present invention provides methods for the synthesis of a wide range of α-aryl and α-heteroaryl α,α-difluoroketones by palladium-catalyzed coupling of aryl and heteroaryl halides with difluoroacetophenones. The products of these reactions can be converted, in addition to alcohols and amines by standard functional group interconversions, to the corresponding difluoromethylarenes by C—C bond cleavage. The reactions occur with an air-stable palladium catalyst and aryl halide as limiting reagent, thereby constituting a practical method to create a large family of difluoroalkylarene and heteroarene derivatives.

Aromatic compounds containing a fluorine atom or a trifluoromethyl group on an aromatic ring are now widespread in medicinal chemistry (Purser, et al., *Chem. Soc. Rev.*, 2008, 37:320; Wang, et al., *Chem. Rev.*, 2014, 114: 2432). It is well established that fluorine and trifluoromethyl substituents modulate the lipophilicity and metabolic stability of organic compounds; they also alter the non-covalent interactions of the aryl group, providing a method to affect binding affinities and selectivities (Banks, et al., *Organofluorine Compounds: Principles and Commercial Applications*; Plenum: New York, 2000; Kirsch, P., *Modern Fluoroorganic Chemistry*; Wiley-VCH Verlag GmbH & Co. KGaA: Weinheim, 2013). However, compounds containing more complex alkyl groups with fluorine atoms at the benzylic position are less studied because they are challenging to prepare. Reliable methods to form a carbon-carbon bond between an aryl electrophile and a difluoroalkyl nucleophile have not been developed (Feng, et al., *Angew. Chem., Int. Ed.*, 2014, 53:1669).

This limitation on the coupling of aryl electrophiles with fluoroalkyl nucleophiles arises from several properties of fluoroalkyl groups. First, a majority of coupling reactions mediated by transition metal complexes form the aryl-alkyl bond by reductive elimination from an arylmetal alkyl intermediate (Enchavarren, et al., *Metal-Catalyzed Cross-Coupling Reactions*; Meijere, et al., Eds.; WILEY-VCH Verlag GmbH & Co. KGaA: Weinheim, 2008; Vol. 1, p 1), and this reductive elimination is slow when the alkyl group contains fluorine on the carbon. Second, there are few methods to prepare α,α-difluoroalkylmetal reagents (Zemtsov, et al., *J. Org. Chem.*, 2013, 79:818); therefore transition-metal complexes containing an α,α-difluoroalkyl group are rare.

The carbonyl functionality is one of the cornerstones of organic chemistry because it can be transformed into a wide range of functional groups, including alcohols, amines, alkyl groups, and esters. Considering the versatile chemistry of the carbonyl functionality, we considered that an approach to prepare a variety of alkylarenes containing fluorine on the benzylic carbon atom would result from the coupling of aryl halides with fluorinated enolates. This coupling and subsequent derivatization could afford a variety of α-aryl-α,α-difluorocarbonyl compounds. However, the couplings of fluorinated enolates with aryl electrophiles are limited to reactions that require stoichiometric amounts of copper, high temperatures, or both (Fujikawa, et al., *Org. Lett.*, 2011, 13:5560; Guo, et al., *J. Fluorine Chem.* 2012, 143:135). Because of the severity of these reaction conditions, the scope of these coupling reactions is narrow and does not encompass haloarenes containing many of the common functional groups of medicinally important compounds.

SUMMARY OF THE INVENTION

Figure 1:
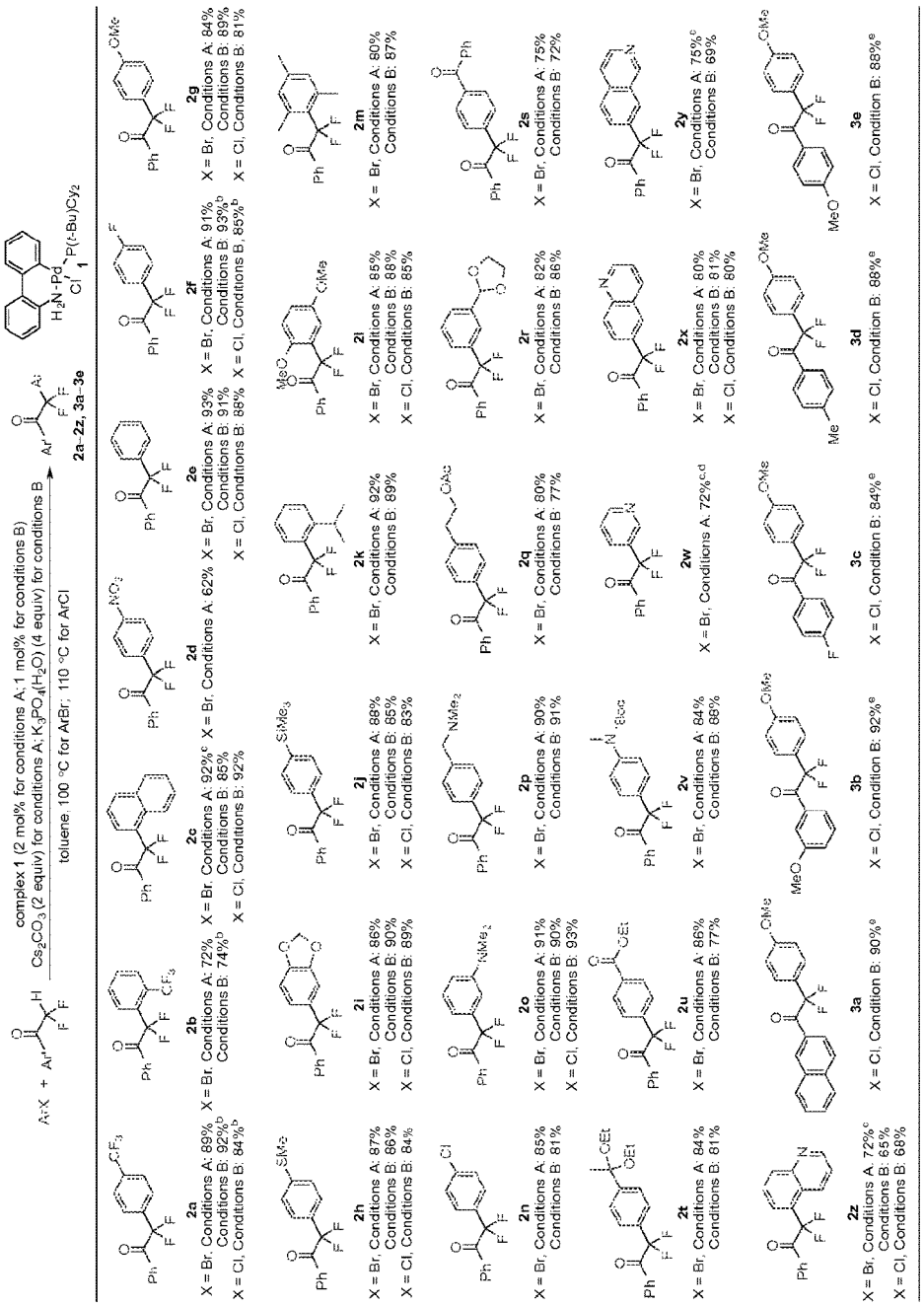
FIG. 1. α-Arylation of α,α-difluoroacetophenone with aryl bromides and chlorides catalyzed by complex 1. Conditions: Conditions A: α,α-difluoroacetophenone (0.400 mmol), aryl bromide (0.800 mmol), $Cs_2CO_3$ (0.800 mmol), complex 1 (8.0 μmol), toluene (1 mL), 100° C., 24 h; Conditions B: aryl bromide or aryl chloride (0.200 mmol), α,α-difluoroacetophenone (0.400 mmol), $K_3PO_4(H_2O)$ (0.800 mmol), complex 1 (2 μmol), toluene (1 mL), 100° C. for aryl bromide and 110° C. for aryl chloride, 30 h; [b]Yields were determined by $^{19}F$ NMR spectroscopy with 1-bromo-4-fluorobenzene as internal standard; [c]complex 1 (20 μmol, 5 mol %); [d]120° C. [e]complex 1 (4 μmol, 2 mol %).

In various embodiments, the present invention provides compositions and methods for coupling of a species with a leaving group (e.g., halide or sulfonate) with an α,α-difluorocarbonyl compound. For example, the invention provides compositions and methods for coupling aryl halides, heteroaryl halides, or vinyl halides with an α,α-difluocarbonyl compound, e.g., α,α-difluroketone or a silyl enol ether thereof.

In an exemplary embodiment, the invention provides a composition comprising: (i) a precursor compound having the formula $R^P$—$X^L$, wherein $R^P$ is a member selected from substituted or unsubstituted aryl, substituted or unsubstituted heteroaryl, and substituted or unsubstituted vinyl; $X^L$ is a leaving group, such as a halogen (e.g., Cl, Br, and I); (ii) an α,α-difluoromethyl carbonyl compound according to Formula I:

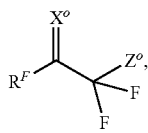

(I)

wherein $R^F$ is a member selected from substituted or unsubstituted aryl, and substituted or unsubstituted heteroaryl, substituted or unsubstituted alkyl and substituted or unsubstituted heteroalkyl. When $R^F$ is substituted or unsubstituted alkyl or substituted or unsubstituted heteroalkyl, this group does not include enolizable hydrogens a to the carbonyl moiety. In various embodiments, $R^F$ is selected from $OR^{z1}$, $SR^{z1}$ and $NR^{z2}R^{z3}$. $R^{z1}$ is selected from substituted or unsubstituted alkyl, substituted or unsubstituted heteroalkyl, substituted or unsubstituted aryl, substituted or unsubstituted heteroaryl, and acyl. $R^{z2}$ and $R^{z3}$ are independently selected from H, substituted or unsubstituted alkyl, substituted or unsubstituted heteroalkyl, substituted or unsubstituted aryl, substituted or unsubstituted heteroaryl, acyl and sulfonyl. Optionally, $R^{z2}$ and $R^{z3}$, together with the nitrogen to which they are attached, are joined to form a 4-8 membered ring, which is a substituted or unsubstituted heterocycloalkyl or heteroaryl ring system. $X^o$ is O or S. $Z^o$ is H or $Si(R^{30})_3$, in which each $R^{30}$ is independently selected from H, substituted or unsubstituted alkyl or substituted or unsubstituted heteroalkyl substituted or unsubstituted aryl, substituted or unsubstituted heteroaryl substituted or unsubstituted alkoxy, halogen, amino, or two or more of $R^{30}$, together with the Si atom to which they are attached are joined to form a 4-8-membered ring. When $Z^o$ is $Si(R^{30})_3$, the silicon enolate can have Si on the alpha carbon or the oxygen or both as shown below:

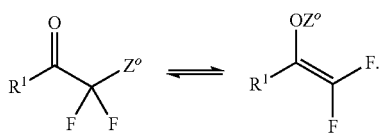

The composition further comprises, (iii) a complex comprising palladium and a ligand. An exemplary complex is $PR^{P1}R^{P2}R^{P3}$ in which $R^{P1}$, $R^{P2}$ and $R^{P3}$ are independently selected from substituted or unsubstituted alkyl, substituted or unsubstituted aryl, alkoxy, amino and a combination thereof. In an exemplary embodiment, in which $R^F$ is substituted or unsubstituted aryl, at least one of the alkyl groups of the trialkylphosphine is not a tertiary alkyl group. In those embodiments in which $R^F$ is selected from substituted or unsubstituted alkyl, substituted or unsubstituted heteroalkyl, substituted or unsubstituted heteroaryl, $OR^{z1}$, and Nee, the ligand is preferably not limited structurally in this manner.

The mixture further comprises, (iv) an organic or inorganic base.

In various embodiments, the invention provides a method of forming a compound having the formula:

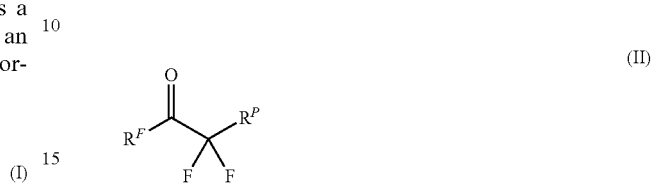

(II)

wherein $R^F$ is a member selected from substituted or unsubstituted aryl, and substituted or unsubstituted heteroaryl, substituted or unsubstituted alkyl and substituted or unsubstituted heteroalkyl. When $R^F$ is substituted or unsubstituted alkyl or substituted or unsubstituted heteroalkyl, this group does not include enolizable hydrogens a to the carbonyl moiety. In various embodiments, $R^F$ is selected from $OR^{z1}$ and $NR^{z2}R^{z3}$. $R^{z1}$ is selected from substituted or unsubstituted alkyl, substituted or unsubstituted heteroalkyl, substituted or unsubstituted aryl, substituted or unsubstituted heteroaryl, and acyl. $R^{z2}$ and $R^{z3}$ are independently selected from H, substituted or unsubstituted alkyl, substituted or unsubstituted heteroalkyl, substituted or unsubstituted aryl, substituted or unsubstituted heteroaryl, acyl and sulfonyl. Optionally, $R^{z2}$ and $R^{z3}$, together with the nitrogen to which they are attached, are joined to form a 4-8 membered ring, which is a substituted or unsubstituted heterocycloalkyl or heteroaryl ring system. $R^P$ is a member selected from substituted or unsubstituted aryl, substituted or unsubstituted heteroaryl, and substituted or unsubstituted vinyl. The method comprising: (a) forming a composition of the invention; and (b) incubating the composition under conditions appropriate to form a compound according to Formula II by coupling the precursor compound with the α,α-difluoroketone or silyl enol ether thereof.

In various embodiments, the invention provides a method of forming a difluoromethyl compound according to Formula III:

(III)

wherein $R^P$ is a member selected from substituted or unsubstituted aryl, substituted or unsubstituted heteroaryl, and substituted or unsubstituted vinyl. The method comprises: (a) forming a composition of the invention; (b) incubating the composition under conditions appropriate to form a compound according to Formula II; and (c) cleaving the compound formed in step (b) with base to form a difluoromethyl compound according to Formula III.

In an exemplary embodiment, the invention provides a method of forming a difluoroacetate according to Formula IV:

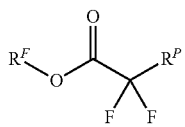

(IV)

wherein $R^F$ is a member selected from substituted or unsubstituted aryl, and substituted or unsubstituted heteroaryl; and $R^P$ is a member selected from substituted or unsubstituted aryl, substituted or unsubstituted heteroaryl, and substituted or unsubstituted vinyl. The method comprises: (a) forming a composition of the invention; (b) incubating the composition under conditions appropriate to form a compound according to Formula II; and (c) reacting the compound formed in step (b) with an oxidizing agent to form said difluoroacetate.

Additional objects, advantages and embodiments of the invention are set forth in the detailed description below.

DETAILED DESCRIPTION OF THE EMBODIMENTS

I. Introduction

The present invention provides a significant improvement in methods of preparing difluoromethyl compounds as well as providing novel difluoromethyl compounds. Aromatic compounds containing a difluoromethyl ($CF_2H$) group are valuable for medicinal chemistry because the difluoromethyl group can act as a bio-isostere of alcohols and thiols and as a lipophilic hydrogen bond donor (Aráoz, et al., Biochemistry, 2000, 39:15971; Hope, H. R., J. Lipid Res., 2000, 41:1604). However, methods for the introduction of the difluoromethyl group onto arenes are limited, and each method has significant limitations.

The most common method to access these difluoromethylarenes is the deoxofluorination of benzaldehydes with sulfur tetrafluoride ($SF_4$) and N,N-diethylaminosulfur trifluoride (DAST) derivatives (Markovskij, et al., Synthesis, 1973, 787; Middleton, W. J., J. Org. Chem., 1975, 40:574; Dolbier, et al., J. Org. Chem., 2008, 73:2469). However, these fluorinating reagents are highly sensitive toward moisture and can undergo explosive decomposition upon heating. Amii's group reported a three-step sequential reaction sequence comprising copper-mediated cross-coupling of aryl iodides with α-silyldifluoroacetates, hydrolysis of the α-aryl difluoroacetates, and decarboxylation of the resulting α-aryl difluoroacetic acids (Fujikawa, et al., Org. Lett., 2011, 13:5560; Fujikawa, et al., Synthesis, 2012, 44:3015). However, in contrast to the methods disclosed herein, these sequential reactions occurred in overall modest yields, required 200° C. for the decarboxylation of α-aryl difluoroesters containing electron-neutral aryl groups and did not occur with those containing electron-rich aryl groups. Baran and coworkers reported a direct introduction of the difluoromethyl group onto heteroarenes with zinc difluoromethanesulfinate (Fujiwara, et al., J. Am. Chem. Soc., 2012, 134:1494). However, reactions with arenes have not been reported thus far, and the regioselectivity for reactions of heteroarenes is distinct from that of halogenated heteroarenes. Finally, the present inventors and Prakash's group recently reported copper-mediated difluoromethylation of aryl iodides with $Me_3SiCF_2H$ and $n-Bu_3SnCF_2H$, respectively, but the scope of these reactions is limited to aryl iodides (Fier, et al., J. Am. Chem. Soc., 2012, 134:5524; Prakash, et al., Angew. Chem., Int. Ed., 2012, 51:12090).

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are intended to be defined as indicated below.

II. Definitions

Where substituent groups are specified by their conventional chemical formulae, written from left to right, the structures optionally also encompass the chemically identical substituents, which would result from writing the structure from right to left, e.g., —CH$_2$O— is intended to also optionally recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10, 12-13}$ linoeyl chain.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —CO$_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above.

Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to optionally include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O) CF$_3$, —C(O)CH$_2$OCH$_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl and heteroaryl groups are generically referred to as "aryl group substituents." The substituents are selected from, for example: H, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are preferably independently selected from hydrogen or substituted or unsubstituted (C$_1$-C$_6$)alkyl. These terms encompass groups considered exemplary "aryl group substituents", which are components of exemplary "substituted aryl" and "substituted heteroaryl" moieties.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non-aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The terms "substrate" and "precursor" are used interchangeably and refer to compound with a leaving group substitutable by a difluoromethyl carbonyl compound in a method and composition of the invention. An exemplary substrate or precursor is a halo-substituted aryl or vinyl compound which can react under the conditions of the invention, to yield at least one product having a difluoromethyl moiety.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein, "electron neutral", "electron donating" and "electron withdrawing" refer to the net electronic effect of substituents on an aryl nucleus. The concept underlying electron neutral, electron donating and electron withdrawing substituents (e.g., aryl group substituents) is well-understood in the art and has been so for many years. Frameworks such as the Crum Brown-Gibson Rule (*J. Chem Soc.* 61, 367 (1892)) and the Hammett Equation (Hammett, Louis P. *J. Am. Chem. Soc.* 59, 96 (1937)) are a useful guide for the selection of individual substituents and combinations of substituents having electron neutral or electron donating properties. The selection of substituted aryl groups functioning within the methods of the invention utilizing the Crum Brown-Gibson Rule and Hammett Rule is a component of the instant invention.

The term "ligand" has the meaning ordinarily ascribed to it in the art. Ligands can include sterically bulky species, such as substituted or unsubstituted aryl, substituted or unsubstituted heteroaryl and substituted or unsubstituted fused ring systems, secondary and tertiary alkyl groups and the like.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

The symbol ～, displayed perpendicular to a bond, indicates the point at which the displayed moiety is attached to the remainder of the molecule.

A "leaving group" has the meaning normally ascribed to this term in the art. Exemplary leaving groups include halides, pseudohalides and phosphates (e.g., OP(O)RR'). Exemplary pseudohalides include sulfonates (e.g., mesylate, tosylate, triflate, etc.). In the exemplary embodiments set forth herein, $X^L$ is a leaving group.

Below are examples of specific embodiments for carrying out the present invention. The examples are offered for illustrative purposes only, and are not intended to limit the scope of the present invention in any way.

In some embodiments, the definition of terms used herein is according to IUPAC.

III. The Compositions

In an exemplary embodiment, the present invention provides a composition comprising: (i) a precursor compound selected from an aryl halide, heteroaryl halide, and vinyl halide, any of which are optionally further substituted; (ii) an α,α-difluoromethyl carbonyl compound, e.g., α,α-difluoroketone or a silyl enol ether thereof; (iii) a complex; and (iv) a base.

The composition functions to couple aryl halides, heteroaryl halides, or vinyl halides of a broad range of structures with α,α-difluoromethyl carbonyl compounds, e.g., α,α-difluoroketones or silyl enol ethers thereof.

In an exemplary embodiment, the invention provides a composition comprising: (i) a precursor compound having the formula $R^P$—$X^L$, wherein $R^P$ is a member selected from substituted or unsubstituted aryl, substituted or unsubstituted heteroaryl, and substituted or unsubstituted vinyl; $X^L$ is a leaving group, such as a halogen (e.g., Cl, Br, and I), sulfonate, etc.; (ii) an α,α-difluoromethyl carbonyl compound according to Formula I:

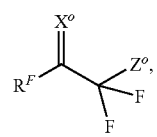

(I)

wherein $R^F$ is a member selected from substituted or unsubstituted aryl, and substituted or unsubstituted heteroaryl, substituted or unsubstituted alkyl and substituted or unsubstituted heteroalkyl. When $R^F$ is substituted or unsubstituted alkyl or substituted or unsubstituted heteroalkyl, this group does not include enolizable hydrogens α to the carbonyl moiety. In various embodiments, $R^F$ is selected from $OR^{z1}$ or $SR^{z1}$ and $NR^{z2}R^{z3}$. $R^{z1}$ is selected from substituted or unsubstituted alkyl, substituted or unsubstituted heteroalkyl, substituted or unsubstituted aryl, substituted or unsubstituted heteroaryl, acyl. $R^{z2}$ and $R^{z3}$ are independently selected from H, substituted or unsubstituted alkyl, substituted or unsubstituted heteroalkyl, substituted or unsubstituted aryl, substituted or unsubstituted heteroaryl, acyl and sulfonyl. Optionally, $R^{z2}$ and $R^{z3}$, together with the nitrogen to which they are attached, are joined to form a 4-8 membered ring, which is a substituted or unsubstituted heterocycloalkyl or heteroaryl ring system. $X^o$ is O or S. $Z^o$ is H or $Si(R^{30})_3$, in which each $R^{30}$ is independently selected from H, substituted or unsubstituted alkyl or substituted or unsubstituted heteroalkyl substituted or unsubstituted aryl, substituted or unsubstituted heteroaryl substituted or unsubstituted alkoxy, halogen, amino, or two or more of $R^{30}$, together with the Si atom to which they are attached are joined to form a 4-8-membered ring. When $Z^o$ is $Si(R^{30})_3$, the silicon enolate can have Si on the alpha carbon or the oxygen or both as shown below:

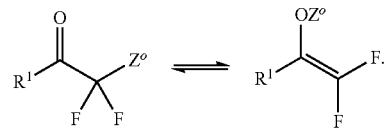

The composition further comprises, (iii) a complex comprising palladium and a ligand. An exemplary complex is $PR^{P1}R^{P2}R^{P3}$ in which $R^{P1}$, $R^{P2}$ and $R^{P3}$ are independently selected from substituted or unsubstituted alkyl, substituted or unsubstituted aryl, alkoxy, amino and a combination thereof. In an exemplary embodiment, in which $R^F$ is substituted or unsubstituted aryl, at least one of the alkyl groups of the trialkylphosphine is not a tertiary alkyl group. In those embodiments in which $R^F$ is selected from substituted or unsubstituted alkyl, substituted or unsubstituted heteroalkyl, substituted or unsubstituted heteroaryl, $OR^{z1}$, $NR^{z2}R^{z3}$, the ligand is preferably not limited structurally in this manner.

The mixture further comprises, (iv) an organic or inorganic base.

IIIa. Precursor Compound

In some embodiments, the precursor compound is a member selected from a halide or a pseudohalide (e.g., a sulfonate). Exemplary precursor compounds include, without limitation, an aryl halide, heteroaryl halide, and vinyl halide, any of which are optionally further substituted (in addition to the halogen moiety).

In some embodiments, the precursor compound has the formula:

wherein $R^P$ is a member selected from substituted or unsubstituted aryl, substituted or unsubstituted heteroaryl, and substituted or unsubstituted vinyl; and $X^L$ is a member selected from Cl, Br, and I.

In some embodiments $X^L$ is Cl. In some embodiments $X^L$ is Br. In some embodiments $X^L$ is I.

In some embodiments, $R^P$ is a substituted or unsubstituted five-membered heteroaryl ring. In some embodiments, $R^P$ is a substituted or unsubstituted six-membered heteroaryl ring.

In some embodiments, the precursor compound has the formula:

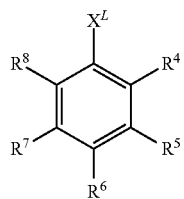

wherein $R^4$, $R^5$, $R^6$, $R^7$, and $R^8$ are independently members selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^9R^{10}$, $-NR^9R^{10}$, $-OR^9$, $-S(O)_2R^9$, $-C(O)R^9$, $-COOR^9$, $-CONR^9R^{10}$, $-S(O)_2OR^9$, $-OC(O)R^9$, $-C(O)NR^9R^{10}$, $-NR^9C(O)R^{10}$, $-NR^9SO_2R^{10}$ and $-NO_2$, wherein two or more of $R^4$, $R^5$, $R^6$, $R^7$ and $R^8$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl. $X^L$ is a member selected from Cl, Br, and I.

The symbols $R^9$ and $R^{10}$ represent members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^9$ and $R^{10}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

In some embodiments, the precursor compound has the formula:

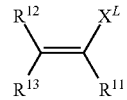

wherein $R^{11}$, $R^{12}$, and $R^{13}$ are independently members selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^9R^{10}$, $-NR^9R^{10}$, $-OR^9$, $-S(O)_2R^9$, $-C(O)R^9$, $-COOR^9$, $-CONR^9R^{10}$, $-S(O)_2OR^9$, $-OC(O)R^9$, $-C(O)NR^9R^{10}$, $-NR^9C(O)R^{10}$, $-NR^9SO_2R^{10}$ and $-NO_2$. Two or more of $R^{11}$, $R^{12}$, and $R^{13}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl. $R^9$ and $R^{10}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^9$ and $R^{10}$, together with the atoms to which they are bonded, are optionally joined to form a 5- to 7-membered ring. $X^L$ is a member selected from Cl, Br, and I.

Examples of the diversity of precursor compounds of use in the compositions and methods of the invention are set forth in Examples appended hereto.

IIIb. α,α-Difluoromethyl Carbonyl Compounds

α,α-Difluoroketone

In some embodiments, the α,α-difluoromethyl carbonyl compound is an α,α-difluoroketone having a structure according to Formula I:

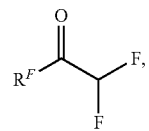

wherein $R^F$ is a member selected from substituted or unsubstituted aryl, and substituted or unsubstituted heteroaryl.

In some embodiments, $R^F$ is substituted or unsubstituted aryl. In some embodiments, $R^F$ is substituted or unsubstituted phenyl. In some embodiments, $R^F$ is substituted or unsubstituted naphthyl. In various embodiments, $R^F$ is substituted or unsubstituted alkyl or substituted or unsubstituted heteroalkyl. When $R^F$ is substituted or unsubstituted alkyl or substituted or unsubstituted heteroalkyl, this group does not include enolizable hydrogens α to the carbonyl moiety.

An exemplary ketone arylation is set forth below:

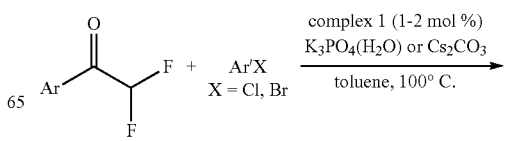

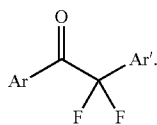

Examples of the diversity of α,α-difluoroketones of use in the compositions and methods of the invention are set forth in the examples appended hereto.

Silyl Enol Ether of an α,α-Difluoroketone

In some embodiments the carbonyl compound is a silyl enol ether of an α,α-difluoroketone. An exemplary silyl enol ether (of an α,α-difluoroketone) has a structure according to Formula V:

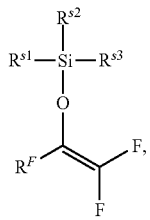

(V)

wherein $R^F$ is a member selected from substituted or unsubstituted alkyl, substituted or unsubstituted heteroaryl, substituted or unsubstituted aryl, and substituted or unsubstituted heteroaryl; and $R^{s1}$, $R^{s2}$, and $R^{s3}$ are independently selected from H, substituted or unsubstituted alkyl, substituted or unsubstituted cycloalkyl, substituted or unsubstituted heteroalkyl, substituted or unsubstituted heterocycloalkyl, substituted or unsubstituted aryl, and substituted or unsubstituted heteroaryl. When $R^F$ is substituted or unsubstituted alkyl or substituted or unsubstituted heteroalkyl, there are no enolizable hydrogens a to the carbonyl.

In some embodiments, $R^F$ is substituted or unsubstituted aryl. In some embodiments, $R^F$ is substituted or unsubstituted phenyl. In some embodiments, $R^F$ is substituted or unsubstituted naphthyl. In various embodiments, $R^F$ is substituted or unsubstituted alkyl or substituted or unsubstituted heteroalkyl. When $R^F$ is substituted or unsubstituted alkyl or substituted or unsubstituted heteroalkyl, this group does not include enolizable hydrogens a to the carbonyl moiety.

In some embodiments, $R^{s1}$, $R^{s2}$, and $R^{s3}$ are independently selected from unsubstituted $C_1$, $C_2$, $C_3$, $C_4$, $C_5$ and $C_6$ alkyl. In some embodiments, one or more of $R^{s1}$, $R^{s2}$, and $R^{s3}$ are methyl. In some embodiments, $R^{s1}$, $R^{s2}$, and $R^{s3}$ are each methyl.

An exemplary arylation of a silicon enolate of a ketone is set forth below:

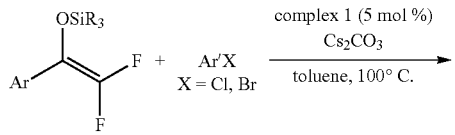

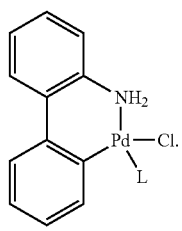

L = P(t-Bu)Cy$_2$, 1
L = P(t-Bu)$_2$Cy, 2

Examples of the diversity of silicon enolates and ketone starting materials of use in the compositions and methods of the invention are set forth in the examples appended hereto.

Silicon Enolates of (C=O) Compounds (Ketones, Amides and Esters)

In various embodiments, the carbonyl compound is a silicon enolate of a carbonyl or carboxylic acid derivative compound. Exemplary C=O-containing compounds include ketones, amides and esters, e.g., compounds according to Formula VI:

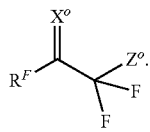

(VI)

In Formula IV, $R^F$ is a member selected from substituted or unsubstituted aryl, substituted or unsubstituted heteroaryl, substituted or unsubstituted alkyl and substituted or unsubstituted heteroalkyl. When $R^F$ is substituted or unsubstituted alkyl or substituted or unsubstituted heteroalkyl, this group does not include enolizable hydrogens a to the carbonyl moiety. In various embodiments, $R^F$ is selected from $OR^{z1}$, $SR^{z1}$ and $NR^{z2}R^{z3}$. $R^{z1}$ is selected from substituted or unsubstituted alkyl, substituted or unsubstituted heteroalkyl, substituted or unsubstituted aryl, substituted or unsubstituted heteroaryl, and acyl. $R^{z2}$ and $R^{z3}$ are independently selected from H, substituted or unsubstituted alkyl, substituted or unsubstituted heteroalkyl, substituted or unsubstituted aryl, substituted or unsubstituted heteroaryl, acyl and sulfonyl. Optionally, $R^{z2}$ and $R^{z3}$, together with the nitrogen to which they are attached, are joined to form a 4-8 membered ring, which is a substituted or unsubstituted heterocycloalkyl or heteroaryl ring system. $Z^o$ is $Si(R^{30})_3$, in which each $R^{30}$ is independently selected from H, substituted or unsubstituted alkyl, or substituted or unsubstituted heteroalkyl, substituted or unsubstituted aryl, substituted or unsubstituted heteroaryl, substituted or unsubstituted alkoxy, halogen, amino Two or more of $R^{30}$, together with the Si atom to which they are attached are optionally joined to form a 4-8-membered ring. $X^o$ is O or S. As one of skill in the art will appreciate, the instant method is also of use to form nitriles and other carboxylic acid derivatives.

An exemplary arylation of a silicon enolate of an amide is set forth below:

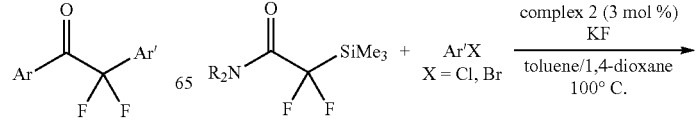

-continued

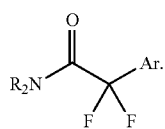

Examples of the diversity of silicon enolates and amide starting materials of use in the compositions and methods of the invention are set forth in the examples appended hereto.

IIIc. Complex

In some embodiments, the complex comprises a metal and a ligand. In some embodiments, the complex is generated in situ from a metal source and a ligand or ligand source. In some embodiments, the complex is not generated in situ. In some embodiments, the metal is palladium.

Exemplary sources of palladium for generating the catalyst in situ are palladium alkene complexes, such as palladium dibenzylidene acetone of varying metal-alkene rations, palladium acetate, and palladacyclic complexes, e.g.,

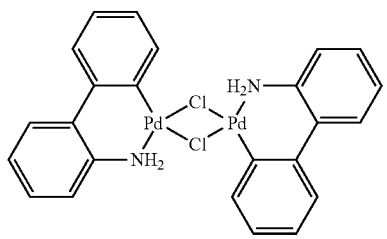

The palladacycle precursor (lacking the phosphine ligand) can be prepared as described in Albert, J.; Granell, J.; Zafrilla, J.; Font-Bardia, M.; Solans, X. *J. Organomet. Chem.* 2005, 690 (2), pp. 422-429.

An exemplary complex is $PR^{P1}R^{P2}R^{P3}$ in which $R^{P1}$, $R^{P2}$ and $R^{P3}$ are independently selected from substituted or unsubstituted alkyl, substituted or unsubstituted aryl, alkoxy, amino and a combination thereof. In an exemplary embodiment, in which $R^F$ is substituted or unsubstituted aryl, at least one of the alkyl groups of the trialkylphosphine is not a tertiary alkyl group. In those embodiments in which $R^F$ is selected from substituted or unsubstituted alkyl, substituted or unsubstituted heteroalkyl, substituted or unsubstituted heteroaryl, $OR^{z1}$, $NR^{z2}R^{z3}$, the ligand is preferably not limited structurally in this manner.

In some embodiments the ligand comprises a trialkylphosphine moiety. In some embodiments, at least one of the alkyl groups of the trialkylphosphine moiety is not a tertiary alkyl group. In some embodiments the alkyl groups of the trialkylphosphine moiety are independently selected from $C_1$, $C_2$, $C_3$, $C_4$, $C_5$, $C_6$, or $C_7$ alkyl and $C_3$, $C_4$, $C_5$, $C_6$, or $C_7$ cycloalkyl. In some embodiments the alkyl groups of the trialkylphosphine moiety are independently selected from tert-butyl and cyclohexyl.

In some embodiments, the complex has the formula:

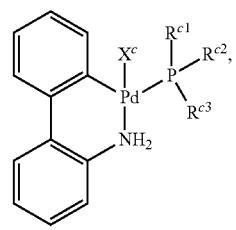

wherein $X^c$ is a formally anionic ligand (often called X-type), such as halide, sulfonates (e.g., methanesulfonate), and nitrate; and $R^{c1}$, $R^{c2}$, and $R^{c3}$ are independently selected from substituted or unsubstituted branched hydrocarbon (e.g., tert-butyl) and substituted or unsubstituted carbocycle (e.g., cyclohexyl).

In some embodiments, $X^c$ is a member selected from halogen, sulfonates, and nitrate. In some embodiments, $X^c$ is halogen. In some embodiments, $X^c$ is Cl. In some embodiments, $X^c$ is a sulfonate. In some embodiments, $X^c$ is methanesulfonate.

In some embodiments, the complex has a formula selected from:

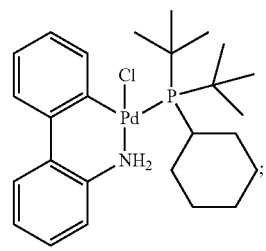

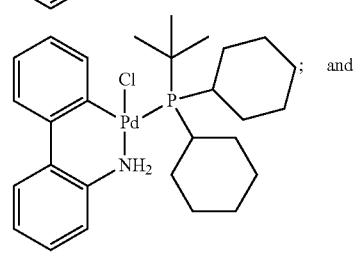

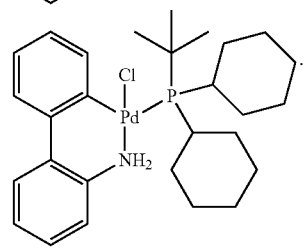

In some embodiments, the complex is present in the composition in an amount of less than 10 mol % relative to the α,α-difluoromethyl carbonyl compound. In some embodiments, complex is present in said composition in an amount of about 2 mol % to about 5 mol % relative to the α,α-difluoromethyl carbonyl compound. In some embodiments, complex is present in said composition in an amount of about 2 mol % relative to the α,α-difluoromethyl carbonyl compound. In some embodiments, complex is present in said composition in an amount of about 5 mol % relative to the silyl enol ether.

In various embodiments, the complex comprises palladium and a ligand, wherein the ligand comprises a phosphorus ligand with the formula $PR^F{}_3$, wherein, when $R^F$ is substituted or unsubstituted aryl, alkyl, alkoxy, or amino, at least one of the alkyl groups of said phosphine composition in which $PR^F{}_3$ is a trialkylphosphine is not a tertiary alkyl.

In an exemplary embodiment, in which the complex is a trialkylphosphine, the precursor compound is other than substituted or unsubstituted acetophenone.

IIId. Base

In some embodiments, the base can be any base strong enough to deprotonate the α,α-difluoromethyl carbonyl compound while not decomposing the α,α-difluoromethyl carbonyl compound. In some embodiments the base is insoluble in the solvent. In some embodiments the base is only partially soluble in the solvent.

In some embodiments, the base is a member selected from $Cs_2CO_3$ and $K_3PO_4$. In some embodiments, the base is $Cs_2CO_3$.

IIIe. Solvent

In some embodiments, the composition further comprises a solvent. The solvent can be any compound or mixture of compounds useful to dissolve at least a portion of one or more component of the composition. In some embodiments, the solvent is a non-polar, organic solvent, such as toluene. In some embodiments, the solvent is toluene.

IIIf. Exemplary Compositions

Any of the combinations of precursor compound, α,α-difluoromethyl carbonyl compound or silicon enolate thereof, complex, base, and, optionally, solvent are encompassed by this disclosure and specifically provided by the invention.

In an exemplary embodiment, the composition does not contain an organotin reagent. In an exemplary embodiment, the composition does not contain $Bu_3SnF$. In an exemplary embodiment, when the composition comprises a silicon enolate of an α,α-difluoroketone, the composition does not contain an organotin reagent. In an exemplary embodiment, when the composition comprises a silicon enolate of an α,α-difluoromethyl carbonyl compound the composition does not contain $Bu_3SnF$.

In an exemplary embodiment, the precursor compound, the α,α-difluoromethyl carbonyl compound, and the base are present in the composition in a molar ratio of about 2:1:2. In an exemplary embodiment, the precursor compound, the α,α-difluoromethyl carbonyl compound, and the base are present in the composition in a molar ratio of about 2:1:4. In an exemplary embodiment, the precursor compound, the α,α-difluoromethyl carbonyl compound, and the base are present in the composition in a molar ratio of about 1:2:2.

IV. The Methods

Coupling Reaction

In various embodiments, the invention provides a method of forming a compound having the formula:

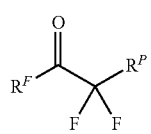

(II)

wherein $R^F$ is a member selected from substituted or unsubstituted aryl, and substituted or unsubstituted heteroaryl, substituted or unsubstituted alkyl and substituted or unsubstituted heteroalkyl. When $R^F$ is substituted or unsubstituted alkyl or substituted or unsubstituted heteroalkyl, this group does not include enolizable hydrogens α to the carbonyl moiety. In various embodiments, $R^F$ is selected from $OR^{z1}$ and $NR^{z2}R^{z3}$. $R^{z1}$ is selected from substituted or unsubstituted alkyl, substituted or unsubstituted heteroalkyl, substituted or unsubstituted aryl, substituted or unsubstituted heteroaryl, and acyl. $R^{z2}$ and $R^{z3}$ are independently selected from H, substituted or unsubstituted alkyl, substituted or unsubstituted heteroalkyl, substituted or unsubstituted aryl, substituted or unsubstituted heteroaryl, acyl and sulfonyl. Optionally, $R^{z2}$ and $R^{z3}$, together with the nitrogen to which they are attached, are joined to form a 4-8 membered ring, which is a substituted or unsubstituted heterocycloalkyl or heteroaryl ring system. $R^P$ is a member selected from substituted or unsubstituted aryl, substituted or unsubstituted heteroaryl, and substituted or unsubstituted vinyl.

The method includes: (a) forming a composition of the invention; and (b) incubating the composition under conditions appropriate to form a compound according to Formula II by coupling the precursor compound with the α,α-difluoromethyl carbonyl compound (e.g., α,α-difluoroketone or silyl enol ether thereof) as shown below.

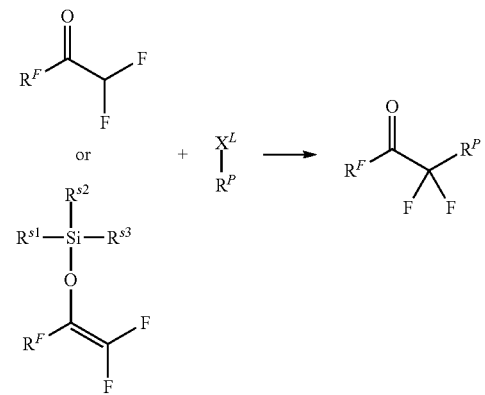

Scheme A. Exemplary reaction scheme illustrating the coupling reaction.

According to an exemplary method of the invention, any useful temperature or range of temperatures can be used to convert the precursor to the desired product. In an exemplary embodiment, the composition is incubated at a temperature from about 20° C. (room temperature) to about 120° C., e.g., from about 80° C. to about 120° C., e.g., about 100° C.

The reaction mixture can be incubated for any useful length of time. In various embodiments, the invention is incubated at a desired temperature for about 1 minute to about 48 hours, e.g., for about 6 hours to about 42 hours, e.g., for about 12 hours to about 36 hours, e.g., for about 18 hours to about 30 hours, e.g. for about 24 hours.

The reaction mixture can be incubated in a vessel of any useful configuration. In an exemplary embodiment, the vessel is sealed while the reaction mixture is incubated, e.g., a sealed tube.

Ketone Cleavage

In various embodiments, the present invention provides methods for forming a difluoromethyl compound having a structure according to Formula III:

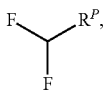

(III)

wherein $R^P$ is a member selected from substituted or unsubstituted aryl, substituted or unsubstituted heteroaryl, and substituted or unsubstituted vinyl; said method comprising: (a) forming a composition disclosed herein; (b) incubating said composition under conditions appropriate to form a compound according to Formula II; and (c) cleaving the compound formed in step (b) with base to form the difluoromethyl compound.

In some embodiments, the base in step (c) is aqueous KOH. In some embodiments, step (c) is performed in situ.

Formation of Carboxylic Acids, and Derivatives

In an exemplary embodiment, the invention provides a method for forming a carboxylic acid or a derivative of a carboxylic acid, e.g, acid halide, aldehyde, ketone, anhydride or a nitrile by further reaction of an ester or amide prepared by a method of the invention. Methods of forming such derivatives are well-known in the art.

Baeyer-Villiger Oxidation

In various embodiments, the present invention provides methods for forming a difluoroacetate having a structure according to Formula VIII:

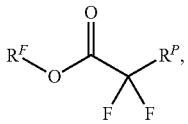

(VIII)

wherein $R^F$ is a member selected from substituted or unsubstituted aryl, and substituted or unsubstituted heteroaryl; and $R^P$ is a member selected from substituted or unsubstituted aryl, substituted or unsubstituted heteroaryl, and substituted or unsubstituted vinyl; said method comprising: (a) forming a composition disclosed herein; (b) incubating said composition under conditions appropriate to form a compound having a structure according to Formula II:

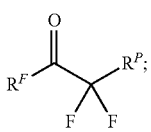

(II)

and (c) reacting the compound formed in step (b) with an oxidizing agent to form the difluoroacetate.

The oxidizing agent is an organic or inorganic oxidizing agent. In some embodiments, the oxidizing agent is mCPBA.

In some embodiments, the method further comprises the step of filtering the composition between steps (b) and (c).

The following examples illustrate embodiments of the invention and are not intended to limit the scope of the compositions of the invention or the methods in which they find use.

EXAMPLES

Example 1

Scheme 1

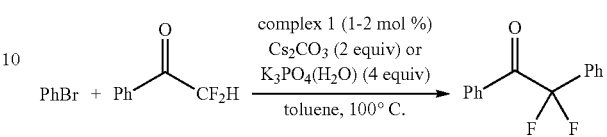

Conditions A: NMR yield: 94%
limiting reagent: ketone, 2 mol % of 1, $Cs_2CO_3$
Conditions B: NMR yield: 93%
limiting reagent: PhBr, 1 mol % of 1, $K_3PO_4(H_2O)$ The direct arylation of α,α-difluoroacetophenone with bromobenzene shown in Scheme 1 was selected as a model reaction to identify an active Pd-catalyst and reaction components to conduct this transformation under relatively mild conditions. This reaction was tested with Pd-catalysts generated from 5 mol % of $Pd(dba)_2$ and a range of bisphosphines (BINAP, BIPHEP, DPPF, and DCPF) and monophosphines ($PCy_3$, $P(t-Bu)Cy_2$, $P(t-Bu)_2Cy$, $P(t-Bu)_3$, $P(t-Bu)_2Ph$, $P(t-Bu)Ph_2$, $PCy_2Ph$, $PAd_2(n-Bu)$, SPhos, and Q-Phos) in the presence of relatively weak base $Cs_2CO_3$ at 80° C. The reaction catalyzed by the combination of $Pd(dba)_2$ (5 mol %) and the rarely utilized phosphine $P(t-Bu)Cy_2$ or $PAd_2(n-Bu)$ (6 mol %) afforded the coupled product in 84% yield; the same reaction with $P(t-Bu)Cy_2$ as ligand at 100° C. afforded the coupled product in 95% yield.

To render the catalyst convenient to use, a single-component palladacyclic complex 1 containing $P(t-Bu)Cy_2$ as the dative ligand was prepared. Similar palladacyclic precursors have been used for C—C and C—N cross-coupling reactions (Kinzel, et al., *J. Am. Chem. Soc.*, 2010, 132: 14073; Bruno, et al., *Org. Lett.*, 2013, 15:2876; Bruno, et al., *Chemical Science*, 2013, 4:916). The model reaction occurred in high yields in the presence of 1-2 mol % of complex 1 as catalyst and $Cs_2CO_3$ as base with ketone as the limiting reagent (Conditions A) or in the presence of $K_3PO_4$ ($H_2O$) as base with bromobenzne as the limiting reagent (Conditions B) in toluene at 100° C. (Scheme 1).

Selected results of these studies on the reaction scope are summarized in FIG. 1. These reactions were conducted under two sets of conditions with limiting ketone or limiting haloarene (conditions A and conditions B, as in Scheme 1). In general, a wide range of electronically varied aryl bromides and aryl chlorides underwent this cross-coupling process with α,α-difluoroacetophenone in high yields. Reactions of aryl chlorides afforded the coupled products in yields that were comparable to those of reactions of the corresponding aryl bromides under conditions B (2a, 2c, 2e-2j, 2l, 2h, 2x and 2z).

These arylation reactions tolerate a range of functionalities, including nitro (2d), ether (2g, 2i, and 2l), thioether (2h), ester (2q and 2u), non-enolizable ketone (2s), and carbamate (2v) moieties. Reactions of substrates bearing both bromo- and chloro-substituents occurred selectively at the bromide (2n), leaving the C—Cl bond intact and accessible for further functionalization. Free hydroxyl, aniline, amine, cyano, enolizable ketone, or aldehyde functionalities are not compatible with the reaction conditions. However, aryl bromides containing a dimethylamino (2o), dimethylaminomethyl (2p) group, protected alcohol (2q), protected aldehyde (2r), or protected enolizable ketone (2t) coupled with α,α-difluoroacetophenone in high yields. The scope of the reaction also encompassed α,α-difluoroacetophenones containing a variety of electronically varied aryl groups (reactions of aliphatic ketones $RCH_2C(O)CF_2H$ so far occur at the non-fluorinated methylene position). The reactions of these ketones with 4-chloroanisole were conducted under conditions B with 2 mol % of complex 1, and the coupled products (3a-3e in FIG. 1) were isolated in high yields (84-92%).

The coupling of difluoroacetophenone also occurred with brominated nitrogen-containing heterocycles, such as bromopyridine, quinolines, and isoquinoline (2w-2z). For these reactions a higher catalyst loading (5 mol %) (2w, 2y, and 2z with conditions A) and temperature (120° C.) (2w) were used to obtain good yields of the coupled products.

These coupling reactions can be conducted without a drybox and on a larger scale. The coupling of α,α-difluoroacetophenone with 2-(3-bromophenyl)-1,3-dioxolane conducted outside a drybox on a 2 mmol scale catalyzed by only 0.5 mol % of complex 1 occurred in similarly high yield (89%) as the reaction conducted inside a drybox on a smaller scale (2r, Table 1). Thus, these reactions should be practical for a number of applications in medicinal chemistry.

The α-aryl-α,α-difluoroacetophenone products of the coupling process undergo reactions characteristic of typical carbonyl functionality. For example, they undergo nucleophilic addition of Grignard reagents to form tertiary alcohols, and they are reduced by $NaBH_4$ to afford primary alcohols. Of particular interest, the C—C bond adjacent to the carbonyl group in these ketones can be readily cleaved to afford difluoromethylarenes ($ArCF_2H$).

Arylation of α,α-Difluoroketones

Herein, we present a convenient and efficient method for palladium catalyzed direct coupling of α,α-difluoroketones with aryl halides. A well-defined, single component, moisture and air stable complex 1 is used as a precatalyst, in loading as low as about 2 mol %. High yields for a coupling of a broad range of α,α-difluoroketones and aryl bromides are obtained under developed conditions. Scope of the reaction was further extended for less reactive aryl chlorides, what in some cased required increase of catalyst loading to 5 mol %. Interestingly, methodology proved successful for N-heterocylic aryl bromides, such as pyridine, quinoline and isoquinoline derivatives—substrates of particular importance for medicinal chemistry. Mechanistic investigations revealed that the rate of the model reaction is independent on bromobenzene and catalyst concentration, yet being first order in the ketone and the amount of used base. This unusual observation, together with other mechanistic findings, strongly suggests that the overall rate of the process is mostly determined by the rate of ketone deprotonation.

General Procedure for Acylation of α,α-Difluoroketones

Conditions A:

In a drybox, a 4-mL screw-capped vial was charged with complex 1 (4.5 mg, 8.0 μmol), α,α-difluoroacetophenone (62.5 mg, 0.400 mmol), aryl bromide (0.800 mmol), $Cs_2CO_3$ (260 mg, 0.800 mmol), toluene (1 mL), and a magnetic stirring bar. The vial was sealed with a cap containing a PTFE septum and removed from the drybox. The reaction mixture was stirred at 100° C. for 24 h and then cooled to room temperature. The mixture was quenched with $H_2O$ (0.5 mL) and extracted with $Et_2O$ (3×3 mL). To the ethereal extract, silica (4 mL) was added, and all the volatile materials were evaporated under reduced pressure. The crude product was purified with a CombiFlash system with 5-70% ethyl acetate in hexanes as eluent. The conditions for chromatography and data for characterization of the products are given below.

Conditions B:

In a drybox, a 4-mL screw-capped vial was charged with complex 1 (1.2 mg, 2.0 μmol), aryl bromide or aryl chloride (0.200 mmol), 2,2-difluoro-1-phenylethan-1one (0.400 mmol), $K_3PO_4(H_2O)$ (0.800 mmol), a magnetic stirring bar, and toluene (1.0 mL). The vial was sealed with a cap containing a PTFE septum and removed from the drybox. The reaction mixture was stirred at 100° C. (for reactions of aryl bromides) or 110° C. (for reactions of aryl chlorides) for 30 h and then cooled to room temperature. The mixture was quenched with $H_2O$ (0.5 mL) and extracted with $Et_2O$ (3×3 mL). To the ethereal extract, silica (4 mL) was added, and all the volatile materials were evaporated under reduced pressure. The crude product was purified with a CombiFlash system with 2-20% ethyl acetate in hexanes as eluent. The conditions for chromatography and data for characterization of the products are given below.

Reaction Scope
TABLE 1
Reaction of 2,2-difluoro-1-phenyl-ethanone with aryl bromides[a]
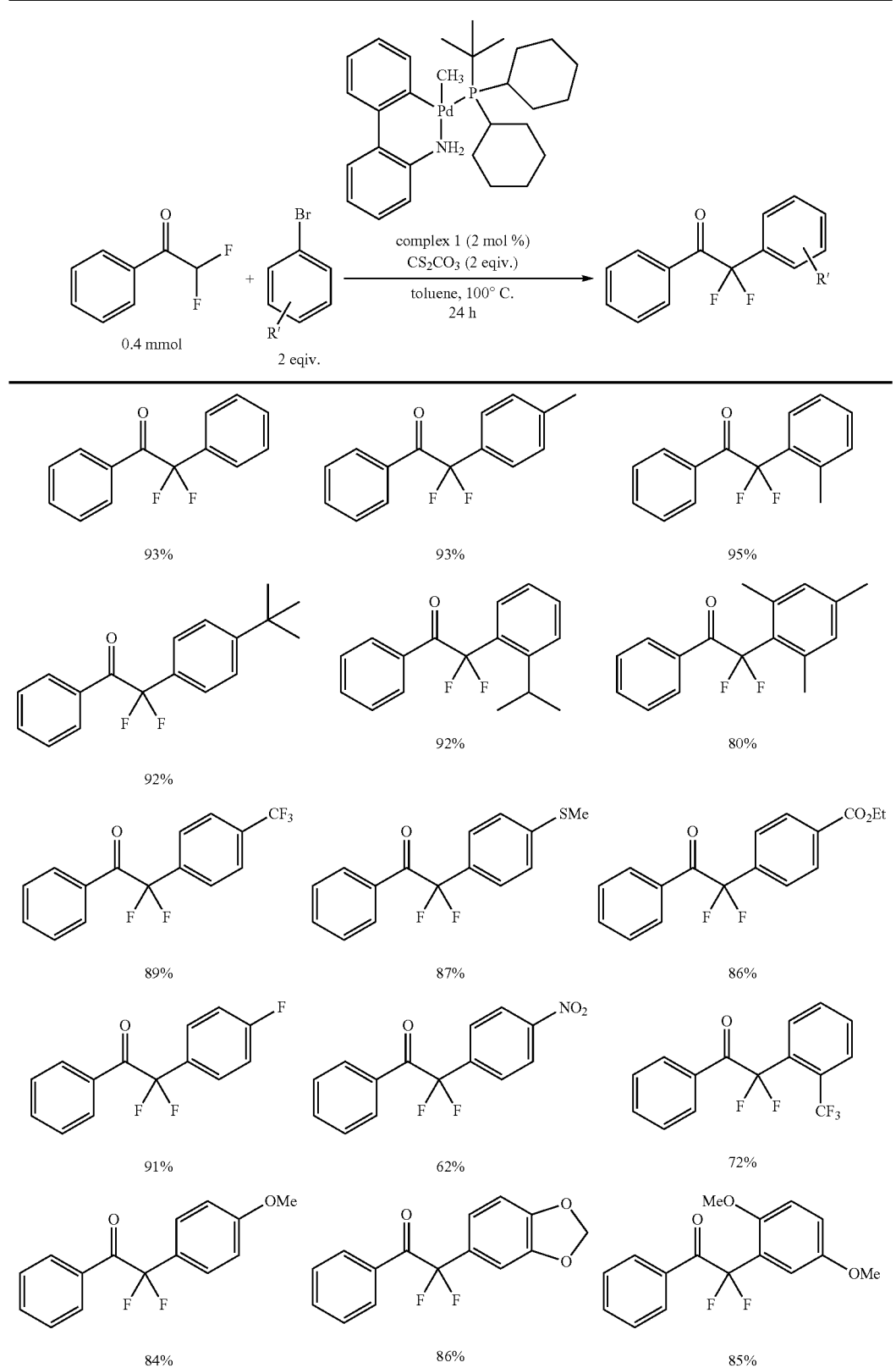

TABLE 1-continued
Reaction of 2,2-difluoro-1-phenyl-ethanone with aryl bromides[a]
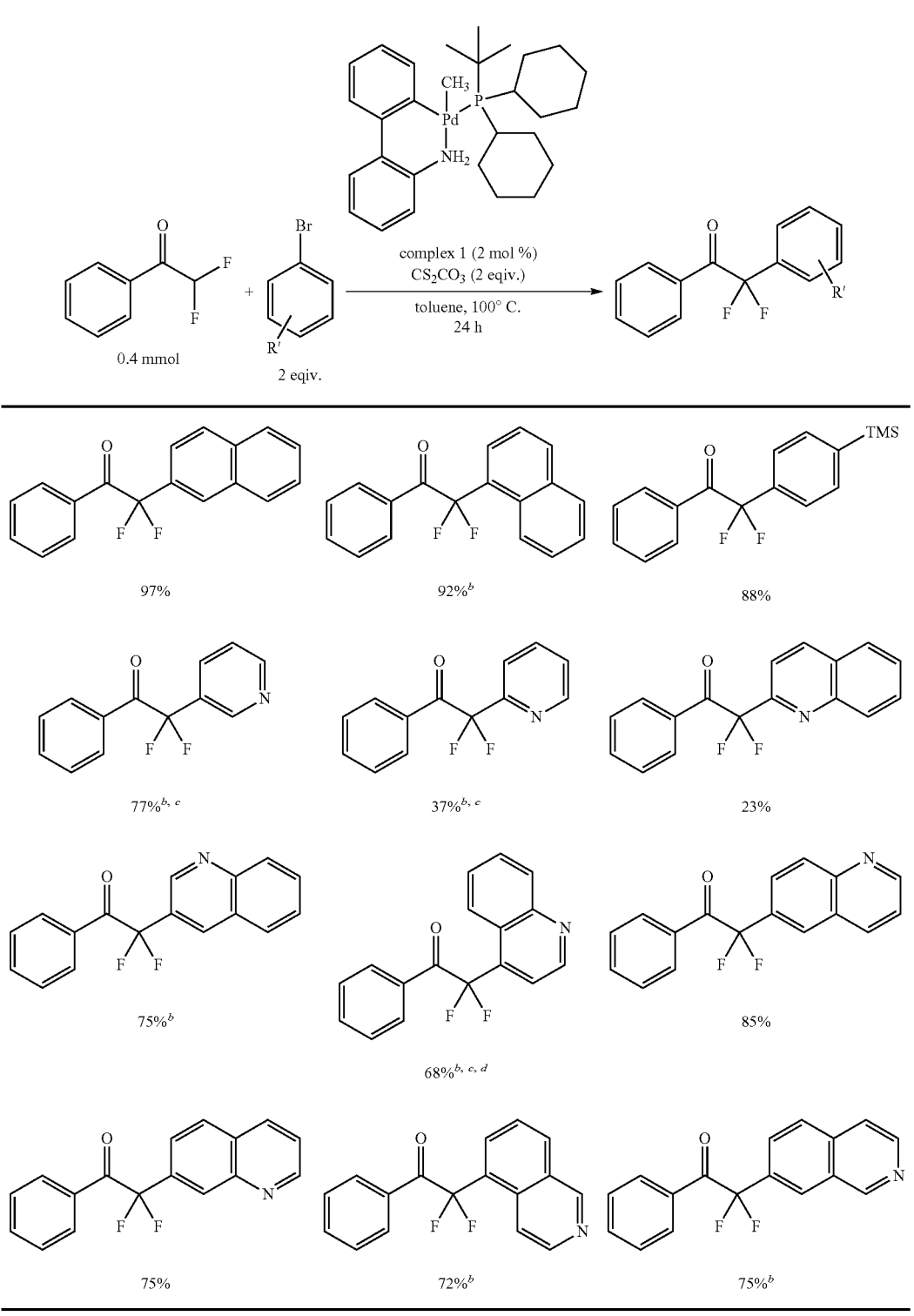
[a]Conditions: 2,2-difluoro-1,2-diphenylethanone (0.4 mmol), aryl bromide (0.8 mmol), Cs$_2$CO$_3$ (0.8 mmol), complex 1 (0.008 mmol, 2 mol %) in toluene (1 mol) at 100° C. for 24 h;
[b]5 mol % of complex 1 was used;
[c]run at 120° C.;
[d]cont. ca 36 mol % of difluoromethyl substituted byproduct.

TABLE 2
Reaction of α,α-difluoroketones with aryl bromides[a]
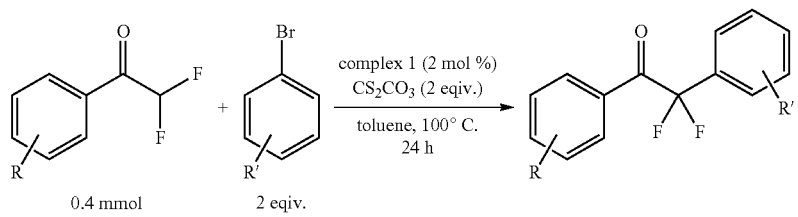
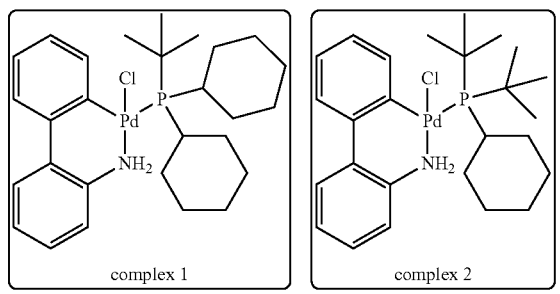
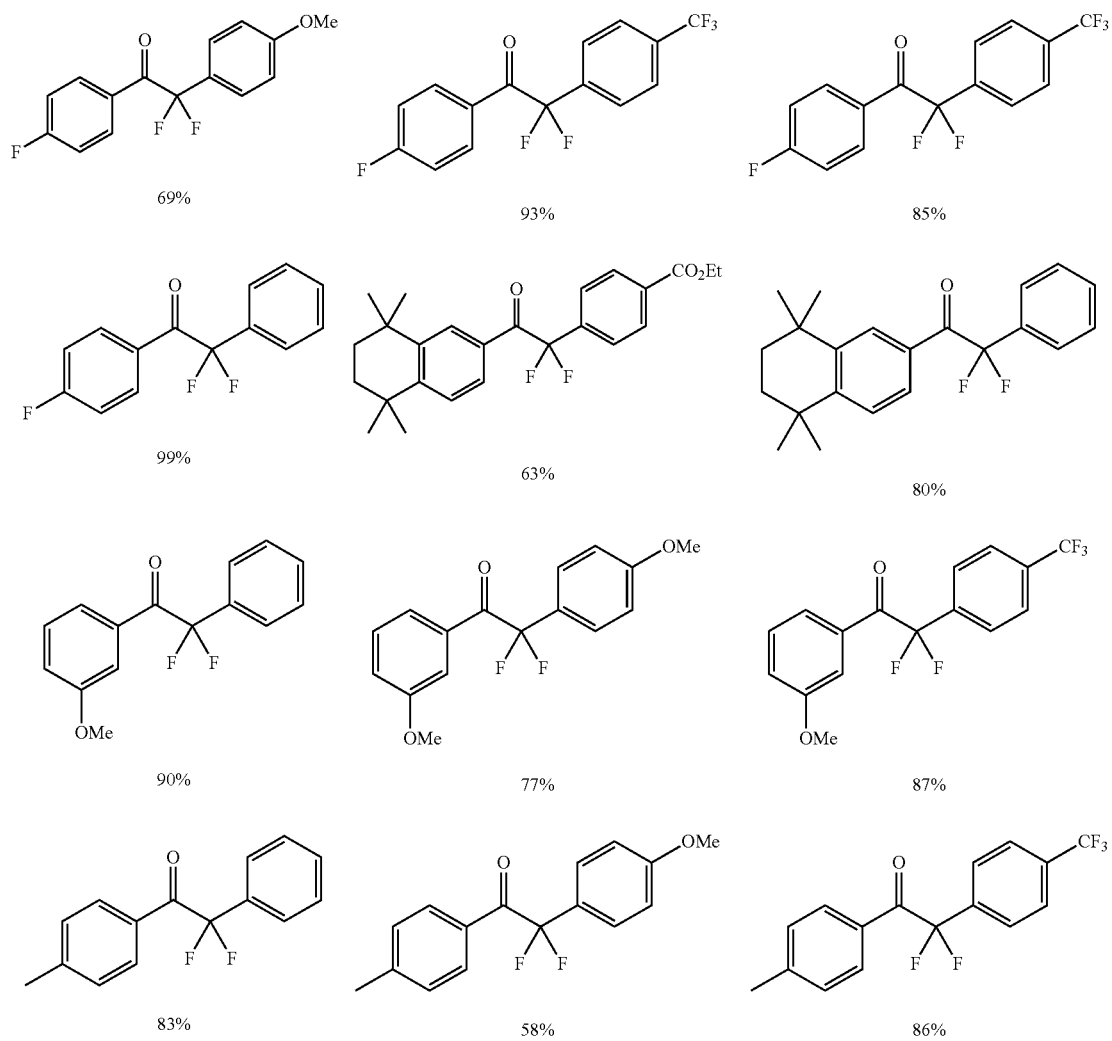

TABLE 2-continued

Reaction of α,α-difluoroketones with aryl bromides[a]

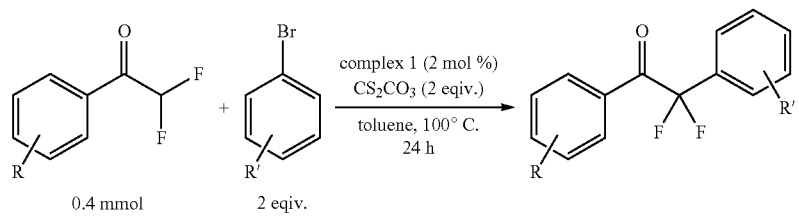

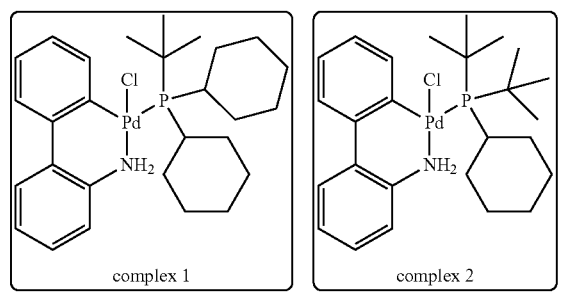

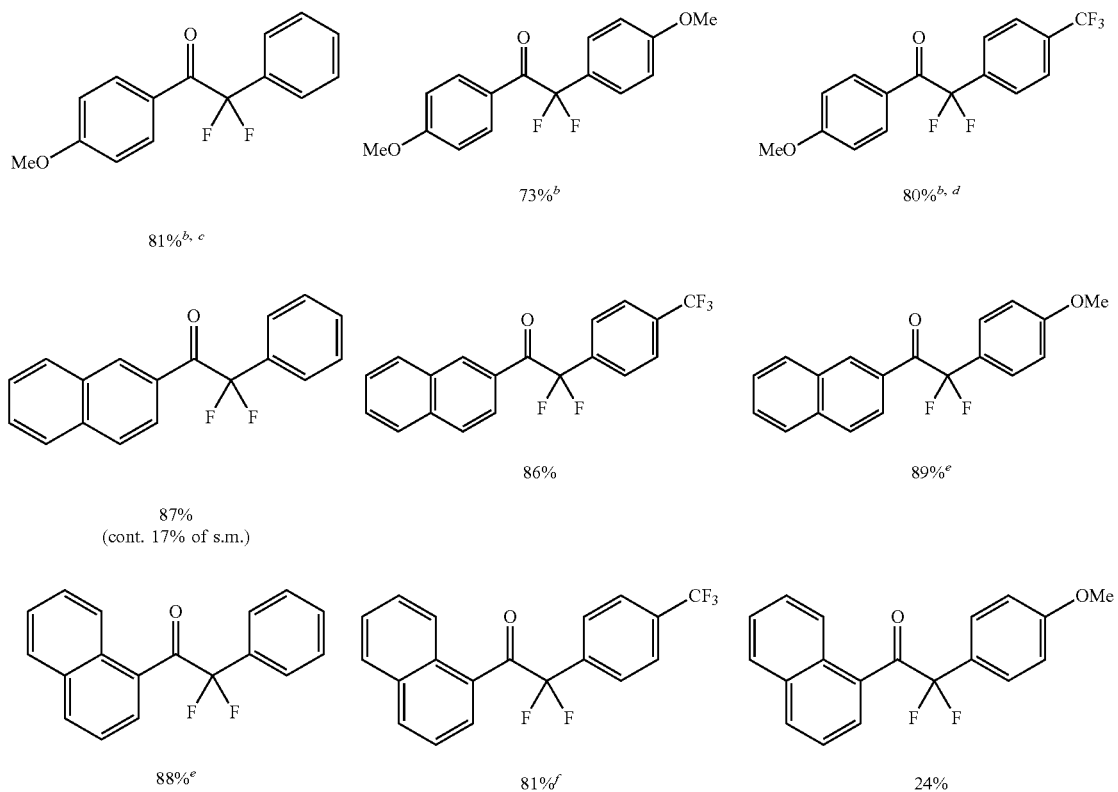

[a]Conditions: α,α-difluoroketone (0.4 mmol), aryl bromide (0.8 mmol), $Cs_2CO_3$ (0.8 mmol), complex 1 (0.008 mmol, 2 mol %) in toluene (1 mol) at 100° C. for 24 h;
[b]4 eqiuv. of $Cs_2CO_3$ (1.6 mmol) used;
[c]contain 5 mol % of starting material;
[d]contain 4 mol % of starting material
[e]5 mol % of complex 2 was used;
[f]5 mol % of complex 1 was used;
[f]contain 20 mol % of starting material.

Representative Examples

2,2-difluoro-1-phenyl-2-(quinolin-3-yl)ethanone

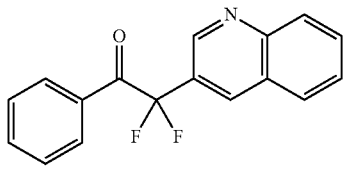 [SMILES: O=C(c1ccccc1)C(F)(F)c1cnc2ccccc2c1]

Starting from 2,2-difluoro-1-phenylethanone (61.8 mg, 0.396 mmol) and 3-bromoquinoline (166 mg, 0.8 mmol) and using 5 mol % of catalyst (11.3 mg, 0.02 mmol) the expected product was isolated as a white solid (75.7 mg, 0.268 mmol, 68%). $^1$H NMR (400 MHz, CDCl$_3$) δ 9.10 (d, J=2.2 Hz, 1H), 8.39 (d, J=0.8 Hz, 1H), 8.15 (d, J=8.5 Hz, 1H), 8.11 (d, J=7.5 Hz, 2H), 7.86 (d, J=8.2 Hz, 1H), 7.83-7.73 (m, 1H), 7.60 (ddd, J=11.0, 5.2, 2.4 Hz, 2H), 7.46 (t, J=7.8 Hz, 2H); $^{19}$F NMR (376 MHz, CDCl$_3$) δ −96.24 (s); $^{13}$C NMR (101 MHz, CDCl$_3$) δ 188.2 (t, J=31.5 Hz), 148.8, 146.9 (t, J=5.5 Hz), 134.6, 134.3 (t, J=6.6 Hz), 131.6, 131.2, 130.3 (t, J=3.0 Hz), 129.4, 128.8, 128.4, 127.6, 126.5, 126.0 (t, J=25.2 Hz), 116.6 (t, J=255.0 Hz).

Coupling of Other Halides

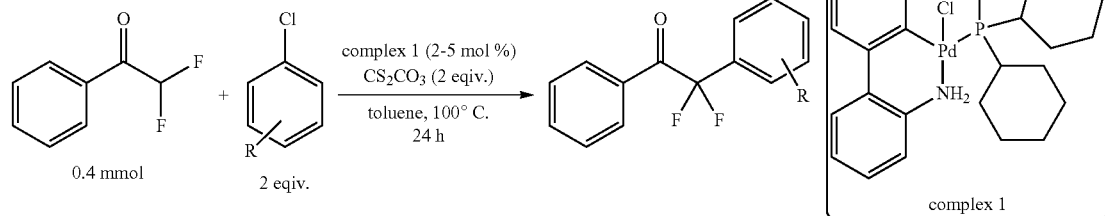

85% (5 mol %)
82% (2 mol %)

90% (5 mol %)
76% (2 mol %)

88% (5 mol %)
37% (2 mol %)

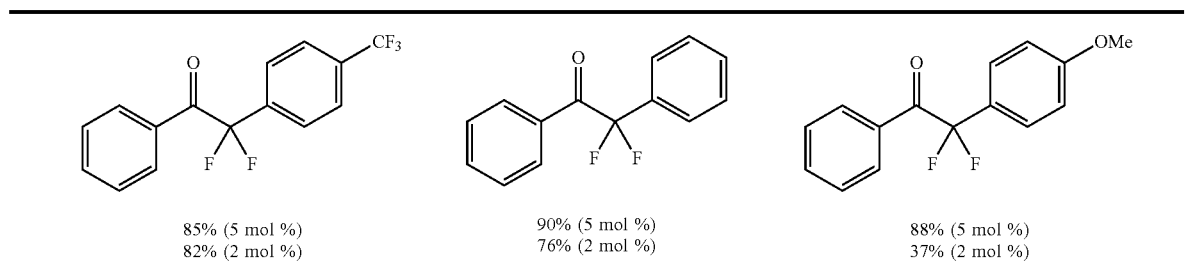

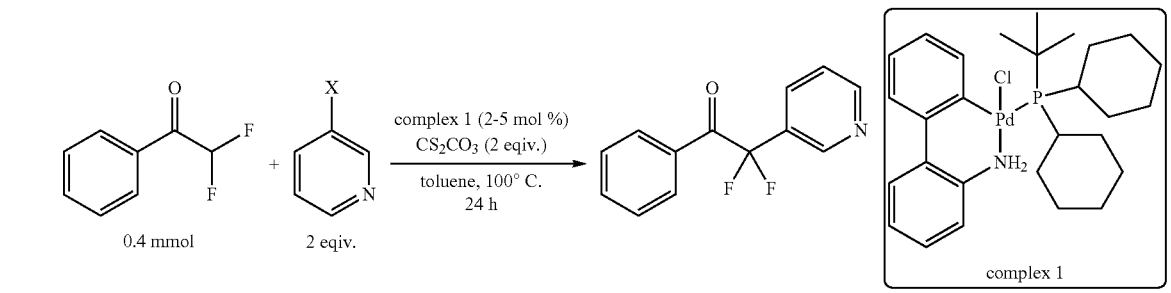

| X | product: s.m. (by $^{19}$F NMR) | isolated yield |
|---|---|---|
| Br | 1:0.42 | 41% |
| I | 1:0.45 | not isolated |

Similar conversion for Br and I substituted pyridine by $^{19}$F NMR. Slightly cleaner reaction for iodide.

2,2-Difluoro-1-phenyl-2-(4-(trifluoromethyl)phenyl)ethanone (2a)

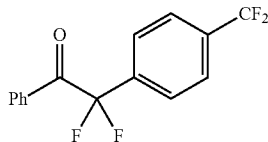

Prepared by coupling of α,α-difluoroacetophenone and 4-bromobenzotrifluoride or 4-chlorobenzotrifluoride under conditions A [yield: 89%] and conditions B [yield: 92% for reaction of aryl bromide and 84% for reaction of aryl chloride]. The title compound was isolated as a white solid after chromatography on silica with a Combiflash system (12 g column, 100:0→98:2 hexanes/EtOAc). $^1$H NMR (400 MHz, CDCl$_3$) δ 8.07 (d, J=7.6 Hz, 2H), 7.75 (s, 4H), 7.63 (t, J=7.4 Hz, 1H), 7.49 (t, J=7.8 Hz, 2H). $^{13}$C {$^1$H} NMR (101 MHz, CDCl$_3$) δ 188.3 (t, J=31.3 Hz), 136.7 (t, J=25.3 Hz), 134.6, 133.0 (q, J=33.2 Hz), 131.7, 130.3 (t, J=2.9 Hz), 128.8, 126.4 (t, J=6.1 Hz), 125.8 (q, J=3.7 Hz), 123.5 (d, J=272.5 Hz), 116.4 (t, J=255.0 Hz). $^{19}$F NMR (376 MHz, CDCl$_3$) δ −63.53 (s), −98.39 (s).

2,2-Difluoro-1-phenyl-2-(2-(trifluoromethyl)phenyl)ethanone (2b)

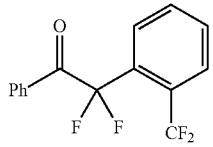

Prepared by coupling of α,α-difluoroacetophenone and 2-bromobenzotrifluoride under conditions A [yield: 72%] and conditions B [yield: 74%]. The title compound was isolated as a yellow liquid after chromatography on silica with a Combiflash system (12 g column, 100:0→98:2 hexanes/EtOAc). $^1$H NMR (400 MHz, CDCl$_3$) δ 8.17 (d, J=7.3 Hz, 2H), 7.82 (d, J=8.1 Hz, 2H), 7.73-7.60 (m, 3H), 7.53 (t, J=7.8 Hz, 2H). $^{13}$C {$^1$H} NMR (101 MHz, CDCl$_3$) δ 188.4 (t, J=33.1 Hz), 134.3, 131.8 (q, J=3.3 Hz), 131.8, 131.2 (t, J=26.4 Hz), 130.9, 130.1 (t, J=2.9 Hz), 128.7, 128.1 (t, J=10.0 Hz), 127.6 (q, J=5.6 Hz), 123.4 (q, J=273.5 Hz), 117.28 (t, J=257.4 Hz). $^{19}$F NMR (376 MHz, CDCl$_3$) δ −58.5 (t, J=11.6 Hz), −94.3 (q, J=11.5 Hz).

2,2-Difluoro-2-(naphthalen-1-yl)-1-phenylethanone (2c)

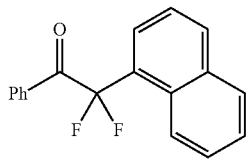 [SMILES: O=C(c1ccccc1)C(F)(F)c1cccc2ccccc12]

Prepared by coupling of α,α-difluoroacetophenone and 1-bromonaphthalene or 1-chloronaphthalene under conditions A [yield: 92%; 5 mol % complex 1 was used] and conditions B [yield: 85% for reaction of aryl bromide and 92% for reaction of aryl chloride]. The title compound was isolated as a yellow liquid after chromatography on silica with a Combiflash system (12 g column, 100:0→98:2 hexanes/EtOAc). $^1$H NMR (400 MHz, CDCl$_3$) δ 8.19 (d, J=8.1 Hz, 1H), 8.13 (d, J=7.7 Hz, 2H), 7.97 (t, J=8.1 Hz, 2H), 7.93-7.83 (m, 1H), 7.65-7.48 (m, 4H), 7.43 (t, J=7.8 Hz, 2H). $^{13}$C {$^1$H} NMR (101 MHz, CDCl$_3$) δ 188.9 (t, J=31.1 Hz), 134.2, 133.9, 132.3, 132.0, 130.3 (t, J=2.4 Hz), 129.7 (t, J=2.0 Hz), 129.2 (t, J=23.1 Hz), 128.8, 128.6, 127.3, 126.3, 125.1 (t, J=9.1 Hz), 124.7 (t, J=2.5 Hz), 124.4, 117.8 (t, J=253.8 Hz). $^{19}$F NMR (376 MHz, CDCl$_3$) δ −94.7 (s). HRMS m/z: calcd for C$_{18}$H$_{12}$F$_2$O: 282.0856. Found 282.0856.

2,2-Difluoro-2-(4-nitrophenyl)-1-phenylethanone (2d)

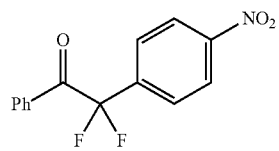

Prepared by coupling of α,α-difluoroacetophenone and 1-bromo-4-nitrobenzene under conditions A [yield: 62%]. The title compound was isolated as a colorless crystalline solid after chromatography on silica with a Combiflash system (12 g column, 100:0→95:5 hexanes/EtOAc). $^1$H NMR (400 MHz, CDCl$_3$) δ 8.33 (d, J=8.9 Hz, 2H), 8.07 (d, J=7.4 Hz, 2H), 7.80 (d, J=8.9 Hz, 2H), 7.68-7.62 (m, 1H), 7.54-7.47 (m, 2H). $^{13}$C {$^1$H} NMR (101 MHz, CDCl$_3$) δ 187.9 (t, J=31.3 Hz), 149.4, 139.1 (t, J=25.3 Hz), 134.8, 131.5 (t, J=1.9 Hz), 130.24 (t, J=3.0 Hz), 128.9, 127.3 (t, J=6.1 Hz), 123.9, 116.3 (t, J=256.1 Hz). $^{19}$F NMR (376 MHz, CDCl$_3$) δ −98.3 (s). HRMS m/z: calcd for C$_{14}$H$_9$F$_2$NO$_3$: 277.0550. Found 277.0554.

2,2-Difluoro-1,2-diphenylethanone (2e)

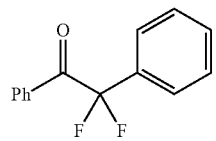 [SMILES: O=C(c1ccccc1)C(F)(F)c1ccccc1]

Prepared by coupling of α,α-difluoroacetophenone and bromobenzene or chlorobenzene under conditions A [yield: 93%] and conditions B [yield: 91% for reaction of aryl bromide and 88% for reaction of aryl chloride]. The title compound was isolated as a colorless oil after chromatography on silica with a Combiflash system (12 g column, 100:0→97:3 hexanes/EtOAc). $^1$H NMR (400 MHz, CDCl$_3$) δ 8.04 (d, J=7.6 Hz, 1H), 7.67-7.55 (m, 2H), 7.51-7.41 (m, 2H). $^{13}$C {$^1$H} NMR (101 MHz, CDCl$_3$) δ 188.9 (t, J=31.0 Hz), 134.2, 133.1 (t, J=25.0 Hz), 132.1, 130.9 (t, J=∼1.6 Hz), 130.2 (t, J=2.9 Hz), 128.8, 128.6, 125.6 (t, J=6.0 Hz), 116.9 (t, J=253.2 Hz). $^{19}$F NMR (376 MHz, CDCl$_3$) δ −98.0 (s). MS (EI): m/z (%): 232 (10), 213 (18), 183 (32), 165 (19), 152 (7), 127 (39), 105 (100), 77 (88), 51 (45). HRMS m/z: calcd for $C_{14}H_{10}F_2O$: 232.0700. Found 232.0694.

2,2-Difluoro-2-(4-fluorophenyl)-1-phenylethanone (2f)

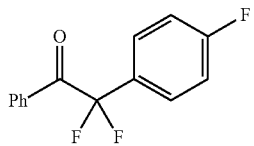 [SMILES: O=C(c1ccccc1)C(F)(F)c1ccc(F)cc1]

Prepared by coupling of α,α-difluoroacetophenone and 1-bromo-4-fluorobenzene or 1-chloro-4-fluorobenzene under conditions A [yield: 91%] and conditions B [yield: 93% for reaction of aryl bromide and 85% for reaction of aryl chloride]. The title compound was isolated as a colorless liquid after chromatography on silica with a Combiflash system (12 g column, 100:0→98:2 hexanes/EtOAc). $^1$H NMR (400 MHz, CDCl$_3$) δ 8.04 (d, J=7.6 Hz, 1H), 7.66-7.56 (m, 1H), 7.46 (t, J=7.8 Hz, 1H), 7.15 (t, J=8.6 Hz, 1H). $^{19}$F NMR (376 MHz, CDCl$_3$) δ −97.0 (s), −109.4 (m). $^{13}$C{$^1$H} NMR (101 MHz, CDCl$_3$) δ 188.7 (t, J=31.4 Hz), 164.1 (d, J=251.2 Hz), 134.3, 131.9, 130.2 (t, J=2.9 Hz), 129.1 (td, J=25.5, 3.3 Hz), 128.7, 128.0 (dt, J=8.8, 6.0 Hz), 116.6 (t, J=253.7 Hz), 116.0 (d, J=22.2 Hz).

2,2-Difluoro-2-(4-methoxyphenyl)-1-phenylethanone (2g)

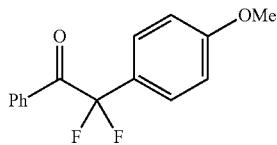 [SMILES: COc1ccc(C(F)(F)C(=O)c2ccccc2)cc1]

Prepared by coupling of α,α-difluoroacetophenone and 4-bromoanisole or 4-chloroanisole under conditions A [yield: 84%] and conditions B [yield: 89% for reaction of aryl bromide and 81% for reaction of aryl chloride]. The title compound was isolated as a colorless liquid after chromatography on silica with a Combiflash system (12 g column, 100:0→00:10 hexanes/EtOAc). $^1$HNMR (400 MHz, CDCl$_3$) δ 8.02 (d, J=7.8 Hz, 2H), 7.58 (t, J=7.5 Hz, 1H), 7.54 (d, J=8.9 Hz, 2H), 7.44 (t, J=7.8 Hz, 2H), 6.96 (d, J=8.7 Hz, 2H), 3.82 (s, 2H). $^{19}$F NMR (376 MHz, CDCl$_3$) δ −96.7 (s). $^{13}$C{$^1$H} NMR (101 MHz, CDCl$_3$) δ 189.1 (t, J=31.5 Hz), 161.4, 134.1, 132.2, 130.2 (t, J=2.8 Hz), 128.6, 127.2 (t, J=5.9 Hz), 125.1 (t, J=25.7 Hz), 117.0 (t, J=252.4 Hz), 114.2, 55.3. MS (EI): m/z (%): 262 (23), 143 (7), 157 (96), 142 (11), 127 (8), 114 (39), 105 (100), 88 (11), 77 (83), 63 (14), 51 (42). FIRMS m/z: calcd for $C_{15}H_{12}F_2O_2$: 262.0805. Found 262.0810.

2,2-Difluoro-2-(4-(methylthio)phenyl)-1-phenylethanone (2h)

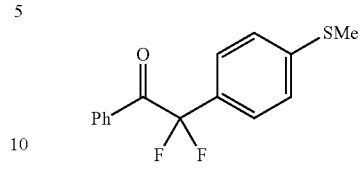

Prepared by coupling of α,α-difluoroacetophenone and 4-bromothioanisole or 4-chlorothioanisole under conditions A [yield: 87%] and conditions B [yield: 86% for reaction of aryl bromide and 84% for reaction of aryl chloride]. The title compound was isolated as a white solid after chromatography on silica with a Combiflash system (12 g column, 100:0→90:10 hexanes/EtOAc). $^1$H NMR (400 MHz, CDCl$_3$) δ 8.03 (d, J=7.9 Hz, 2H), 7.58 (t, J=7.4 Hz, 1H), 7.52 (d, J=8.3 Hz, 2H), 7.44 (t, J=7.8 Hz, 2H), 7.29 (d, J=8.3 Hz, 2H), 2.47 (s, 3H). $^{19}$F NMR (376 MHz, CDCl$_3$) δ −97.7 (s). $^{13}$C{$^1$H} NMR (101 MHz, CDCl$_3$) δ 188.8 (t, J=31.2 Hz), 142.8, 134.2, 132.0, 130.2 (t, J=2.9 Hz), 129.2 (t, J=25.4 Hz), 128.6, 125.9 (t, J=6.0 Hz), 125.7, 116.8 (t, J=253.1 Hz), 14.9. MS (EI): m/z (%) 278 (15), 256 (25), 228 (8), 173 (15), 151 (100), 123 (11), 105 (36), 77 (29), 51 (11). HRMS m/z: calcd for $C_{15}H_{12}F_2OS$: 278.0577. Found 278.0583.

2-(Benzo[d][1,3]dioxol-5-yl)-2,2-difluoro-1-phenylethanone (2i)

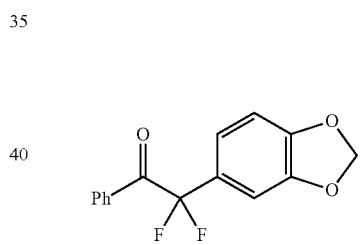

Prepared by coupling of α,α-difluoroacetophenone and 1-bromo-3,4-(methylenedioxy)benzene or 5-chloro-1,3-benzodioxole under conditions A [yield: 86%] and conditions B [yield: 90% for reaction of aryl bromide and 89% for reaction of aryl chloride]. The title compound was isolated as a white solid after chromatography on silica with a Combiflash system (12 g column, 100:0→90:10 hexanes/EtOAc). $^1$H NMR (400 MHz, CDCl$_3$) δ 8.01 (d, J=7.9 Hz, 2H), 7.59 (t, J=7.4 Hz, 1H), 7.44 (t, J=7.8 Hz, 2H), 7.09 (d, J=8.3 Hz, 1H), 7.07 (s, 1H), 6.85 (d, J=8.1 Hz, 1H), 6.00 (s, 2H). $^{19}$F NMR (376 MHz, CDCl$_3$) δ −96.4 (s). $^{13}$C{$^1$H} NMR (101 MHz, CDCl$_3$) δ 188.8 (t, J=31.3 Hz), 149.7, 148.1, 134.2, 132.1, 130.2 (t, J=2.8 Hz), 128.6, 126.7 (t, J=25.6 Hz), 120.1 (t, J=6.7 Hz), 116.7 (t, J=253.3 Hz), 108.5, 106.1 (t, J=6.0 Hz), 101.7. MS (EI): m/z (%): 276 (34), 171 (83), 141 (17), 113 (28), 105 (100), 77 (83), 63 (32), 51 (36). HRMS m/z: calcd for $C_{15}H_{10}F_2O_3$: 276.0598. Found 276.0602.

2,2-Difluoro-1-phenyl-2-(4-(trimethylsilyl)phenyl)ethanone (2j)

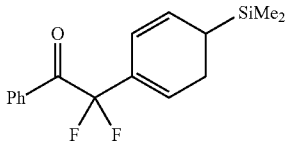

Prepared by coupling of α,α-difluoroacetophenone and 1-bromo-4-(trimethylsilyl)benzene or 1-chloro-4-(trimethylsilyl)benzene under conditions A [yield: 88%] and conditions B [yield: 85% for reaction of aryl bromide and 83% for reaction of aryl chloride]. The title compound was isolated as a colorless liquid after chromatography on silica with a Combiflash system (12 g column, 100:0→98:2 hexanes/EtOAc). $^1$H NMR (400 MHz, CDCl$_3$) δ 8.05 (d, J=7.9 Hz, 2H), 7.67-7.56 (m, 5H), 7.45 (t, J=7.7 Hz, 2H), 0.28 (s, 9H). $^{19}$F NMR (376 MHz, CDCl$_3$) δ -98.2 (s). $^{13}$C{$^1$H} NMR (101 MHz, CDCl$_3$) δ 189.0 (t, J=31.1 Hz), 144.3, 134.2, 133.7, 133.3 (t, J=25.0 Hz), 132.1, 130.3 (t, J=2.8 Hz), 128.6, 124.7 (t, J=5.9 Hz), 117.0 (t, J=253.1 Hz), -1.3. HRMS m/z: calcd for C$_{17}$H$_{18}$F$_2$OSi: 304.1095. Found 304.1100.

2,2-Difluoro-2-(2-isopropylphenyl)-1-phenylethanone (2k)

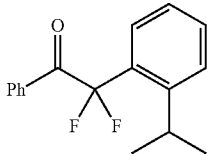

Prepared by coupling of α,α-difluoroacetophenone and 1-bromo-2-isopropylbenzene under conditions A [yield: 92%] and conditions B [yield: 89%]. The title compound was isolated as a colorless oil after chromatography on silica with a Combiflash system (12 g column, 100:0→98:2 hexanes/EtOAc). $^1$H NMR (400 MHz, CDCl$_3$) δ 8.09 (d, J=7.5 Hz, 2H), 7.68-7.58 (m, 2H), 7.46 (dt, J=10.7, 7.5 Hz, 4H), 7.30 (dd, J=11.2, 4.6 Hz, 1H), 3.03 (sept, J=6.8 Hz, 1H), 1.17 (d, J=6.8 Hz, 6H). $^{19}$F NMR (376 MHz, CDCl$_3$) δ -94.1 (s). $^{13}$C{$^1$H} NMR (101 MHz, CDCl$_3$) δ 189.1 (t, J=32.1 Hz), 148.3 (t, J=3.2 Hz), 134.1, 132.4 (t, J=1.8 Hz), 131.1, 130.3 (t, J=22.5 Hz), 130.3 (t, J=2.6 Hz), 128.6, 127.2, 125.8), 125.7 (t, J=9.4 Hz), 117.6 (t, J=253.7 Hz), 30.0, 24.0. HRMS m/z: calcd for C$_{17}$H$_{16}$F$_2$O: 274.1169. Found 274.1174.

2-(2,5-Dimethoxyphenyl)-2,2-difluoro-1-phenylethanone (2l)

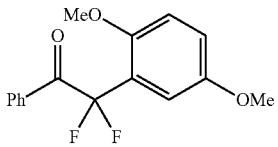 [SMILES: COc1ccc(OC)c(C(F)(F)C(=O)c2ccccc2)c1]

Prepared by coupling of α,α-difluoroacetophenone and 2-bromo-1,4-dimethoxybenzene and 2-chloro-1,4-dimethoxybenzene under conditions A [yield: 85%] and conditions B [yield: 89% for reaction of aryl bromide and 81% for reaction of aryl chloride]. The title compound was isolated as a white solid after chromatography on silica with a Combiflash system (12 g column, 100:0→80:20 hexanes/EtOAc). $^1$H NMR (400 MHz, CDCl$_3$) δ 7.94 (d, J=7.8 Hz, 1H), 7.54 (t, J=7.4 Hz, 1H), 7.40 (t, J=7.8 Hz, 1H), 7.35 (d, J=3.0 Hz, 1H), 6.97 (dd, J=9.0, 2.9 Hz, 1H), 6.79 (d, J=9.0 Hz, 1H), 3.83 (s, 2H), 3.51 (s, 2H). $^{19}$F NMR (376 MHz, CDCl$_3$) δ -98.0 (s). $^{13}$C{$^1$H} NMR (101 MHz, CDCl$_3$) 188.0 (t, J=29.5 Hz), 153.8, 150.6 (t, J=5.3 Hz), 133.5, 132.7, 129.4 (t, J=2.1 Hz), 128.3, 123.9 (t, J=24.0 Hz), 117.5, 114.6 (t, J=251.1 Hz), 113.4, 111.6 (t, J=7.3 Hz), 56.1, 55.8. MS (EI): m/z (%): 292 (54), 187 (65), 172 (8), 157 (10), 139 (32), 129 (12), 114 (13), 109 (20), 105 (100), 101 (14), 77 (68), 63 (7), 51 (20). HRMS m/z: calcd for C$_{16}$H$_{14}$F$_{20}$O$_3$: 292.0911. Found 292.0915.

2,2-Difluoro-2-mesityl-1-phenylethanone (2m)

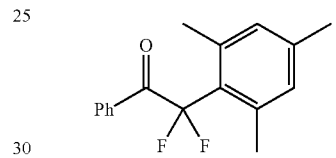

Prepared by coupling of α,α-difluoroacetophenone and 2-bromo-1,3,5-trimethylbenzene under conditions A [yield: 80%] and conditions B [yield: 87%]. The title compound was isolated as a colorless oil after chromatography on silica with a Combiflash system (12 g column, 100:0→98:2 hexanes/EtOAc). $^1$H NMR (400 MHz, CDCl$_3$) δ 8.09 (d, J=7.8 Hz, 2H), 7.62 (t, J=7.4 Hz, 1H), 7.48 (t, J=7.7 Hz, 2H), 6.90 (s, 2H), 2.33 (t, J=4.0 Hz, 6H), 2.30 (s, 3H). $^{19}$F NMR (376 MHz, CDCl$_3$) δ -89.9 (s). $^{13}$C{$^1$H} NMR (101 MHz, CDCl$_3$) δ 189.1 (t, J=33.2 Hz), 139.9, 137.1 (t, J=3.5 Hz), 134.1, 132.4, 131.0, 130.1, 128.6, 127.6 (t, J=21.6 Hz), 119.9 (t, J=254.8 Hz), 22.1 (t, J=5.2 Hz), 20.8. HRMS m/z: calcd for C$_{17}$H$_{16}$F$_2$O: 274.1169. Found 274.1174.

2,2-Difluoro-2-(4-chlorophenyl)-1-phenylethanone (2n)

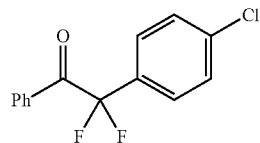 [SMILES: O=C(c1ccccc1)C(F)(F)c1ccc(Cl)cc1]

Prepared by coupling of α,α-difluoroacetophenone and 1-bromo-4-chlorobenzene under conditions A [yield: 85%] and conditions B [yield: 81%]. The title compound was isolated as a colorless oil after chromatography on silica with a Combiflash system (12 g column, 100:0→98:2 hexanes/EtOAc). $^1$H NMR (400 MHz, CDCl$_3$) δ 8.04 (d, J=7.5 Hz, 2H), 7.64-7.58 (m, 1H), 7.55 (d, J=8.6 Hz, 2H), 7.50-7.41 (m, 4H). $^{19}$F NMR (376 MHz, CDCl$_3$) δ -97.8 (s). $^{13}$C{$^1$H} NMR (101 MHz, CDCl$_3$) δ 188.5 (t, J=31.2 Hz), 137.2 (t, J=1.8 Hz), 134.4, 131.9, 131.6 (t, J=25.5 Hz), 130.2

(t, J=2.9 Hz), 129.1, 128.7, 127.2 (t, J=6.0 Hz), 116.6 (t, J=254.1 Hz). MS (EI): m/z (%): 266 (1), 161 (46), 126 (13), 111 (15), 105 (93), 77 (100), 51 (60). HRMS m/z: calcd for $C_{14}H_9F_2OCl$: 266.0310. Found 266.0314.

2-(3-(dimethylamino)phenyl)-2,2-difluoro-1-phenylethan-1-one (2o)

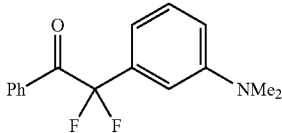

Prepared by coupling of α,α-difluoroacetophenone and 2-bromo-1,4-dimethoxybenzene and 2-chloro-1,4-dimethoxybenzene under conditions A [yield: 91%] and conditions B [yield: 90% for reaction of aryl bromide and 93% for reaction of aryl chloride]. The title compound was isolated as a slightly yellow oil after chromatography on silica with a Combiflash system (12 g column, 100:0→90:10 hexanes/EtOAc). $^1$H NMR (600 MHz, CDCl$_3$) δ 8.03 (d, J=8.0 Hz, 2H), 7.57 (t, J=7.4 Hz, 1H), 7.43 (t, J=7.8 Hz, 2H), 7.30 (t, J=8.0 Hz, 1H), 6.94 (d, J=7.6 Hz, 1H), 6.90 (s, 1H), 6.80 (d, J=8.3 Hz, 1H), 2.96 (s, 6H). $^{13}$C{$^1$H} NMR (151 MHz, CDCl$_3$) δ 189.2 (t, J=30.7 Hz), 150.6, 134.0, 133.9 (t, J=24.3 Hz), 132.4, 130.2 (t, J=2.8 Hz), 129.6, 117.1 (t, J=253 Hz), 114.6, 113.0, 108.7, 40.3. $^{19}$F NMR (565 MHz, CDCl$_3$) δ −98.67. HR-MS (ESI) exact mass calcd for $C_{16}H_{16}F_2NO$: m/z 276.1194 ([M+H]$^+$). Found: 276.1200 ([M+H]$^+$).

2-(4-((dimethylamino)methyl)phenyl)-2,2-difluoro-1-phenylethan-1-one (2p)

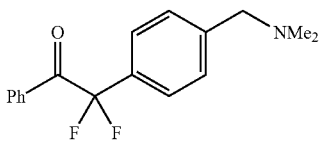 [SMILES: CN(C)Cc1ccc(C(F)(F)C(=O)c2ccccc2)cc1]

Prepared by coupling of α,α-difluoroacetophenone and 1-bromo-4-chlorobenzene under conditions A [yield: 90%] and conditions B [yield: 91%]. The title compound was isolated as a slightly oil after chromatography on silica with a Combiflash system (12 g column, 100:0→90:10 hexanes/Et$_3$N). $^1$H NMR (400 MHz, CDCl$_3$) δ 8.03 (d, J=7.5 Hz, 2H), 7.66-7.51 (m, 3H), 7.51-7.35 (m, 4H), 3.44 (s, 2H), 2.23 (s, 6H). $^{13}$C{$^1$H} NMR (101 MHz, CDCl$_3$) 189.0 (t, J=31.3 Hz), 142.1, 134.2, 132.1, 131.8 (t, J=25.1 Hz), 130.3 (t, J=2.8 Hz), 129.4, 128.6, 125.6 (t, J=5.9 Hz), 116.9 (t, J=253 Hz), 63.8, 45.4. $^{19}$F NMR (376 MHz, CDCl$_3$) δ −96.38. HR-MS (ESI) exact mass calcd for $C_{17}H_{18}F_2NO$: m/z 290.1351 ([M+H]$^+$). Found: 290.1354 ([M+H]$^+$.

4-(1,1-Difluoro-2-oxo-2-phenylethyl)phenethyl acetate (2q)

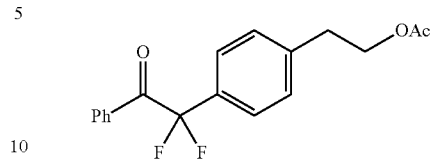

Prepared by coupling of α,α-difluoroacetophenone and 4-bromophenethyl acetate under conditions A [yield: 80%] and conditions B [yield: 77%]. The title compound was isolated as a white solid after chromatography on silica with a Combiflash system (12 g column, 100:0→95:5 hexanes/EtOAc). $^1$H NMR (400 MHz, CDCl$_3$) δ 8.02 (d, J=7.7 Hz, 2H), 7.62-7.52 (m, 3H), 7.43 (t, J=7.8 Hz, 2H), 7.31 (d, J=8.0 Hz, 2H), 4.27 (t, J=6.9 Hz, 2H), 2.96 (t, J=6.9 Hz, 2H), 2.01 (s, 3H). $^{19}$F NMR (376 MHz, CDCl$_3$) δ −97.7 (s). $^{13}$C{$^1$H} NMR (101 MHz, CDCl$_3$) 188.9 (t, J=31.1 Hz), 170.8, 141.0, 134.1, 132.0, 131.3 (t, J=25.2 Hz), 130.2 (t, J=2.8 Hz), 129.3, 128.6, 125.7 (t, J=5.9 Hz), 116.9 (t, J=253.1 Hz), 64.2, 34.7, 20.8. MS (ESI): m/z (%): 341 (100, [M+Na]$^+$), 357 (10, [M+K]$^+$). HRMS (ESI) m/z: calcd for $C_{18}H_{16}F_2O_3Na$: 341.0969. Found 341.0957.

2-(3-(1,3-dioxolan-2-yl)phenyl)-2,2-difluoro-1-phenylethan-1-one (2r)

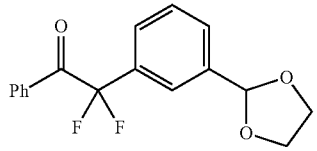 [SMILES: O=C(c1ccccc1)C(F)(F)c1cccc(C2OCCO2)c1]

Prepared by coupling of α,α-difluoroacetophenone and 4-bromophenethyl acetate under conditions A [yield: 82%] and conditions B [yield: 86%]. The title compound was isolated as a white solid after chromatography on silica with a Combiflash system (12 g column, 100:0→90:10 hexanes/EtOAc). $^1$H NMR (600 MHz, CDCl$_3$) δ 8.03 (d, J=7.8 Hz, 2H), 7.77 (s, 1H), 7.61 (d, J=7.9 Hz, 2H), 7.58 (t, J=7.4 Hz, 1H), 7.48 (t, J=7.7 Hz, 1H), 7.44 (t, J=7.9 Hz, 2H), 5.84 (s, 1H), 4.15-4.07 (m, 2H), 4.07-3.98 (m, 2H). $^{13}$C{$^1$H} NMR (151 MHz, CDCl$_3$) δ 188.8 (t, J=30.8 Hz), 139.1, 134.3, 133.3 (t, J=25.0 Hz), 132.1, 130.3 (t, J=2.9 Hz), 129.1, 128.9, 128.7, 126.4 (t, J=6.1 Hz), 123.8 (t, J=6.1 Hz), 116.8 (t, J=253 Hz), 102.9, 65.3. $^{19}$F NMR (376 MHz, CDCl$_3$) δ −96.58.

2-(4-Benzoylphenyl)-2,2-difluoro-1-phenylethanone (2s)

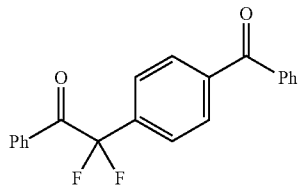 [SMILES: O=C(c1ccccc1)c1ccc(C(F)(F)C(=O)c2ccccc2)cc1]

Prepared by coupling of α,α-difluoroacetophenone and 4'-bromobenzophenone under conditions A [yield: 75%] and conditions B [yield: 72%]. The title compound was isolated as a white solid after chromatography on silica with a Combiflash system (12 g column, 100:0-95:5 hexanes/EtOAc). ¹HNMR (400 MHz, CDCl₃) δ 8.07 (d, J=7.5 Hz, 2H), 7.88 (d, J=8.5 Hz, 2H), 7.83-7.77 (m, 2H), 7.74 (d, J=8.5 Hz, 2H), 7.64-7.57 (m, 2H), 7.52-7.43 (m, 4H). ¹³C{¹H} NMR (101 MHz, CDCl₃) δ 195.6, 188.3 (t, J=31.0 Hz), 139.7, 136.7, 136.5 (t, J=25.0 Hz), 134.4, 132.9, 131.8, 130.2 (d, J=2.8 Hz), 130.1, 130.0, 128.7, 128.4, 125.8 (t, J=6.0 Hz), 116.6 (t, J=254.5 Hz). ¹⁹F NMR (376 MHz, CDCl₃) δ −98.3 (s). MS (EI): m/z (%): 336 (11), 231 (8), 203 (22), 183 (6), 152 (6), 126 (24), 105 (100), 77 (84), 51 (27). HRMS m/z: calcd for C₂₁H₁₄F₂O₂: 336.0962. Found 336.0970.

2-(4-(1,1-diethoxyethyl)phenyl)-2,2-difluoro-1-phenylethan-1-one (2t)

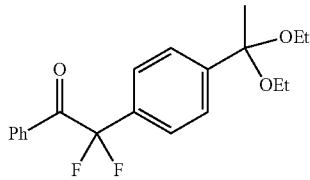 [SMILES: CCOC(C)(OCC)c1ccc(C(F)(F)C(=O)c2ccccc2)cc1]

Prepared by coupling of α,α-difluoroacetophenone and 1-bromo-4-(1,1-diethoxyethyl)benzene under conditions A [yield: 84%] and conditions B [yield: 81%]. The title compound was isolated as a colorless oil after chromatography on silica with a Combiflash system (12 g column, 100:0→95:5 hexanes/EtOAc). ¹H NMR (400 MHz, CDCl₃) δ 8.04 (d, J=7.9 Hz, 2H), 7.69-7.54 (m, 5H), 7.45 (t, J=7.8 Hz, 2H), 3.57-3.43 (m, 2H), 3.42-3.26 (m, 2H), 1.54 (s, 3H), 1.21 (t, J=7.1 Hz, 6H). ¹³C{¹H} NMR (101 MHz, CDCl₃) δ 189.0 (t, J=31.0 Hz), 146.9, 134.2, 132.1 (t, J=25.0 Hz), 131.9, 130.3 (t, J=2.9 Hz), 128.6, 126.5, 125.4 (t, J=5.9 Hz), 117.0 (t, J=252 Hz), 100.9, 56.8, 27.0, 15.2. ¹⁹F NMR (376 MHz, CDCl₃) δ −96.35 (s).

Ethyl 4-(1,1-difluoro-2-oxo-2-phenylethyl)benzoate (2u)

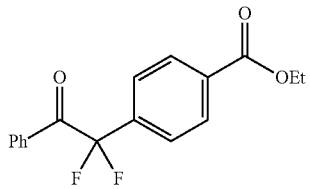 [SMILES: CCOC(=O)c1ccc(C(F)(F)C(=O)c2ccccc2)cc1]

Prepared by coupling of α,α-difluoroacetophenone and ethyl 4-bromobenzoate under conditions A [yield: 86%] and conditions B [yield: 77%]. The title compound was isolated as a colorless oil after chromatography on silica with a Combiflash system (12 g column, 100:0→95:5 hexanes/EtOAc). ¹H NMR (400 MHz, CDCl₃) δ 8.13 (d, J=8.4 Hz, 2H), 8.03 (d, J=7.6 Hz, 2H), 7.68 (d, J=8.4 Hz, 2H), 7.60 (t, J=7.4 Hz, 1H), 7.45 (t, J=7.8 Hz, 2H), 4.39 (q, J=7.1 Hz, 2H), 1.39 (t, J=7.1 Hz, 3H). ¹⁹F NMR (376 MHz, CDCl₃) δ −98.6 (s). ¹³C{¹H} NMR (101 MHz, CDCl₃) δ 188.3 (t, J=30.9 Hz), 165.5, 137.1 (t, J=25.0 Hz), 134.4, 132.8, 131.8, 130.2 (t, J=2.9 Hz), 129.9, 128.7, 125.8 (t, J=6.0 Hz), 116.5 (t, J=254.4 Hz), 61.4, 14.2. MS (ED: m/z (%): 304 (0.3), 259 (33), 199 (14), 183 (6), 171 (16), 154 (13), 143 (16), 126 (32), 105 (99), 77 (100), 51 (40). HRMS m/z: calcd for C₁₇H₁₄F₂O₃: 3045.0911. Found 3045.0906.

tert-Butyl (4-(1,1-difluoro-2-oxo-2-phenylethyl)phenyl)(methyl)carbamate (2v)

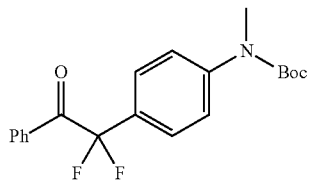 [SMILES: CN(C(=O)OC(C)(C)C)c1ccc(C(F)(F)C(=O)c2ccccc2)cc1]

Prepared by coupling of α,α-difluoroacetophenone and ethyl 4-bromobenzoate under conditions A [yield: 84%] and conditions B [yield: 88%]. The title compound was isolated as a white solid after chromatography on silica with a Combiflash system (12 g column, 100:0→80:20 hexanes/EtOAc). ¹H NMR (400 MHz, CDCl₃) δ 8.06 (d, J=7.5 Hz, 2H), 7.69-7.56 (m, 3H), 7.55-7.44 (m, 2H), 7.41 (d, J=8.6 Hz, 2H), 3.31 (s, 3H), 1.50 (s, 9H). ¹³C{¹H} NMR (101 MHz, CDCl₃) δ 188.9 (t, J=31.1 Hz), 154.3, 146.1, 134.3, 132.1, 130.3 (t, J=2.7 Hz), 129.4 (t, J=25.3 Hz), 128.7, 126.1 (t, J=5.9 Hz), 125.1, 116.8 (t, J=253 Hz), 81.0, 37.0, 28.4. ¹⁹F NMR (376 MHz, CDCl₃) δ −96.97 (s). HR-MS (ESI) exact mass calcd for C₂₀H₂₁F₂NO₃Na: m/z 384.1382 ([M+Na]⁺). Found: 384.1381 ([M+Na]⁺).

2,2-Difluoro-1-phenyl-2-(pyridin-3-yl)ethanone (2w)

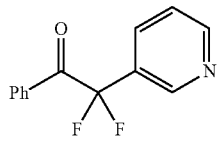 [SMILES: O=C(c1ccccc1)C(F)(F)c1cccnc1]

Prepared by coupling of α,α-difluoroacetophenone and ethyl 4-bromobenzoate under conditions A [yield: 77%, about 90% purity; 5 mol % complex 1 was used and the reaction was conducted at 120° C.]. The title compound was isolated as a yellow oil after chromatography on silica with a Combiflash system (12 g column, 100:0→80:20 hexanes/EtOAc). ¹H NMR (400 MHz, CDCl₃) δ 8.86 (d, J=1.2 Hz, 1H), 8.73 (d, J=4.7 Hz, 1H), 8.13-8.01 (m, 2H), 7.89 (d, J=8.0 Hz, 1H), 7.63 (tt, J=7.4, 1.2 Hz, 1H), 7.48 (t, J=7.8 Hz, 2H), 7.43-7.38 (m, 1H). ¹⁹F NMR (376 MHz, CDCl₃) δ −98.5 (s). ¹³C{¹H} NMR (101 MHz, CDCl₃) δ 188.1 (t, J=31.5 Hz), 151.9, 147.2 (t, I=6.6 Hz), 134.6, 133.8 (t, J=5.9 Hz), 131.6, 130.2 (t, J=3.0 Hz), 129.0 (t, J=25.3 Hz), 128.8, 123.3, 116.4 (t, J=255.0 Hz). HRMS m/z: calcd for C₁₃H₉F₂NO: 233.0652. Found 233.0658.

2,2-Difluoro-1-phenyl-2-(quinolin-6-yl)ethanone (2x)

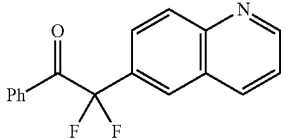 [SMILES: O=C(c1ccccc1)C(F)(F)c1ccc2ncccc2c1]

Prepared by coupling of α,α-difluoroacetophenone and 6-bromoquinoline and 6-chloroquinoline under conditions A [yield: 80%] and conditions B [yield: 81% for reaction of aryl bromide and 80% for reaction of aryl chloride]. The title compound was isolated as a white solid after chromatography on silica with a Combiflash system (12 g column, 100:0→85:15 hexanes/EtOAc). $^1$H NMR (400 MHz, CDCl$_3$) δ 8.96 (dd, J=4.2, 1.5 Hz, 1H), 8.18 (t, J=7.5 Hz, 2H), 8.11-8.01 (m, 3H), 7.89 (dd, J=8.9, 1.9 Hz, 1H), 7.56 (t, J=7.4 Hz, 1H), 7.46-7.37 (m, 3H). $^{19}$F NMR (376 MHz, CDCl$_3$) δ −97.4 (s). $^{13}$C{$^1$H} NMR (101 MHz, CDCl$_3$) δ 188.6 (t, J=31.1 Hz), 152.1, 148.7, 136.7, 134.4, 131.8, 131.1 (t, J=25.1 Hz), 130.5, 130.2 (t, J=2.9 Hz), 128.7, 127.4, 126.2 (t, J=6.8 Hz), 125.1 (t, J=5.2 Hz), 122.0, 116.8 (t, J=254.1 Hz). HRMS m/z: calcd for C$_{17}$H$_{11}$F$_2$NO: 283.0809. Found 283.0814.

2,2-Difluoro-2-(isoquinolin-7-yl)-1-phenylethanone (2y)

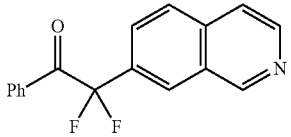 [SMILES: O=C(c1ccccc1)C(F)(F)c1ccc2ccncc2c1]

Prepared by coupling of α,α-difluoroacetophenone and 7-bromoisoquinoline under conditions A [yield: 75%; 5 mol % complex 1 was used] and conditions B [yield: 69%]. The title compound was isolated as a white solid after chromatography on silica with a Combiflash system (12 g column, 100:0-00:30 hexanes/EtOAc). $^1$H NMR (400 MHz, CDCl$_3$) δ 9.31 (s, 1H), 8.60 (d, J=5.7 Hz, 1H), 8.25 (s, 1H), 8.08 (d, J=7.9 Hz, 2H), 7.90 (d, J=8.6 Hz, 1H), 7.84 (d, J=8.7 Hz, 1H), 7.66 (d, J=5.7 Hz, 1H), 7.59 (t, J=7.4 Hz, 1H), 7.45 (t, J=7.8 Hz, 2H). $^{19}$F NMR (376 MHz, CDCl$_3$) δ −97.6 (s). $^{13}$C{$^1$H} NMR (101 MHz, CDCl$_3$) δ 188.5 (t, J=31.3 Hz), 153.1, 144.7, 136.5, 134.5, 131.9 (t, J=25.2 Hz), 131.8, 130.2 (t, J=2.9 Hz), 128.7, 127.6, 127.5, 126.7 (t, J=5.2 Hz), 125.7 (t, J=7.0 Hz), 120.2, 116.7 (t, J=254.5 Hz). FIRMS, m/z: calc'd for C$_{17}$H$_{11}$F$_2$NO: 283.0809. Found 283.0813.

2,2-Difluoro-2-(isoquinolin-5-yl)-1-phenylethanone (2z)

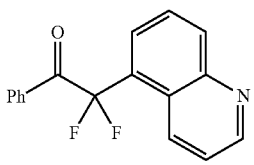 [SMILES: O=C(c1ccccc1)C(F)(F)c1cccc2ncccc12]

Prepared by coupling of α,α-difluoroacetophenone and 5-bromoisoquinoline and 5-chloroisoquinoline under conditions A [yield: 72%; 5 mol % complex 1 was used] and conditions B [yield: 65% for reaction of aryl bromide and 68% for reaction of aryl chloride]. The title compound was isolated as a white solid after chromatography on silica with a Combiflash system (12 g column, 100:0→90:10 hexanes/EtOAc). $^1$H NMR (400 MHz, CDCl$_3$) δ 9.29 (s, 1H), 8.56 (d, J=6.1 Hz, 1H), 8.10 (d, J=7.8 Hz, 4H), 7.85 (d, J=6.0 Hz, 1H), 7.67 (t, J=7.8 Hz, 1H), 7.60 (t, J=7.4 Hz, 1H), 7.46 (t, J=7.8 Hz, 2H). $^{19}$F NMR (376 MHz, CDCl$_3$) δ −95.3 (s). $^{13}$C{$^1$H} NMR (101 MHz, CDCl$_3$) δ 188.3 (t, J=31.3 Hz), 153.2, 144.2, 134.5, 132.5, 131.8, 131.4, 130.3 (t, J=2.6 Hz), 129.0 (t, J=8.7 Hz), 128.7 128.5 (t, J=23.8 Hz), 126.0, 117.5, 117.3 (t, J=255.1 Hz). HRMS m/z: calcd for C$_{17}$H$_{11}$F$_2$NO: 283.0809. Found 283.0811.

2,2-Difluoro-2-(4-methoxyphenyl)-1-(naphthalen-2-yl)ethanone (3a)

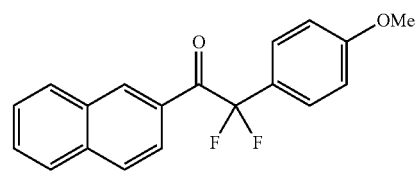 [SMILES: COc1ccc(C(F)(F)C(=O)c2ccc3ccccc3c2)cc1]

Prepared by coupling of 2,2-difluoro-1-(naphthalen-2-yl)ethan-1-one and 4-chloroanisole under conditions B [yield: 90%; 2 mol % complex 1 was used]. The title compound was isolated as a white solid after chromatography on silica with a Combiflash system (12 g column, 100:0→90:10 hexanes/EtOAc). $^1$H NMR (400 MHz, CDCl$_3$) δ 8.62 (s, 1H), 8.06 (d, J=8.5 Hz, 1H), 7.92 (d, J=8.1 Hz, 1H), 7.85 (t, J=8.3 Hz, 2H), 7.65-7.58 (m, 3H), 7.54 (t, J=7.5 Hz, 1H), 6.97 (d, J=8.8 Hz, 2H), 3.80 (s, 3H). $^{13}$C{$^1$H} NMR (101 MHz, CDCl$_3$) δ 189.0 (t, J=31.3 Hz), 161.4, 135.7, 132.9 (t, J=3.7 Hz), 132.1, 129.9, 129.4, 129.2, 128.4, 127.6, 127.2 (t, J=5.9 Hz), 126.9, 125.3 (t, J=25.7 Hz), 124.9, 117.3 (t, J=252.5 Hz), 114.2, 55.2. $^{19}$F NMR (376 MHz, CDCl$_3$) δ −95.9 (s). HRMS m/z: calcd for C$_{189}$H$_{14}$F$_2$O$_2$: 312.0962. Found 312.0963.

2,2-Difluoro-1-(3-methoxyphenyl)-2-(4-methoxyphenyl)ethan-1-one (3b)

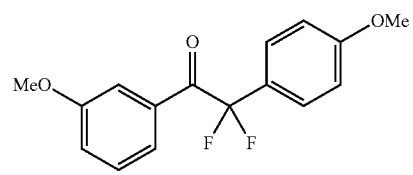 [SMILES: COc1ccc(C(F)(F)C(=O)c2cccc(OC)c2)cc1]

Prepared by coupling of 2,2-difluoro-1-(3-methoxyphenyl)ethan-1-one and 4-chloroanisole under conditions B [yield: 92%; 2 mol % complex 1 was used]. The title compound was isolated as a colorless oil after chromatography on silica with a Combiflash system (12 g column, 100:0→90:10 hexanes/EtOAc). $^1$H NMR (400 MHz, CDCl$_3$) δ 7.60 (d, J=7.7 Hz, 1H), 7.54 (d, J=8.0 Hz, 3H), 7.33 (t, J=8.0 Hz, 1H), 7.12 (dd, J=8.2, 1.9 Hz, 1H), 6.96 (d, J=8.6 Hz, 2H), 3.82 (s, 6H). $^{13}$C{$^1$H} NMR (101 MHz, CDCl$_3$) δ 188.9 (t, J=31.2 Hz), 161.5, 160.0, 133.4, 129.6, 127.2 (t, J=5.9 Hz), 125.2 (t, J=25.7 Hz), 122.9 (t, J=3.5 Hz), 120.7, 117.0 (t, J=252 Hz), 114.4, 114.2, 55.4, 55.3. $^{19}$F NMR (376 MHz, CDCl$_3$) δ −95.31 (s).

2,2-Difluoro-1-(4-fluorophenyl)-2-(4-methoxyphenyl)ethanone (3c)

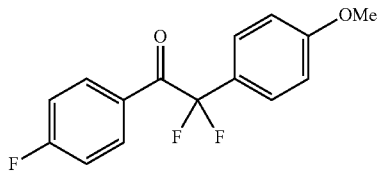 [SMILES: COc1ccc(C(F)(F)C(=O)c2ccc(F)cc2)cc1]

Prepared by coupling of 2,2-difluoro-1-(3-methoxyphenyl)ethan-1-one and 4-chloroanisole under conditions B [yield: 84%; 2 mol % complex 1 was used]. The title compound was isolated as a colorless oil after chromatography on silica with a Combiflash system (12 g column, 100:0→90:10 hexanes/EtOAc). $^1$H NMR (400 MHz, CDCl$_3$) δ 8.07 (dd, J=8.9, 5.4 Hz, 2H), 7.52 (d, J=8.9 Hz, 2H), 7.15-7.07 (m, 2H), 6.96 (d, J=8.9 Hz, 2H), 3.82 (s, 3H). $^{19}$F NMR (376 MHz, CDCl$_3$) δ −96.6 (s), −102.9 (m). $^{13}$C{$^1$H} NMR (101 MHz, CDCl$_3$) 187.6 (t, J=31.8 Hz), 166.2 (d, J=257.6 Hz), 161.5, 133.1 (dt, J=9.6, 3.1 Hz), 128.5, 127.2 (t, J=5.9 Hz), 124.9 (t, J=25.6 Hz), 117.0 (t, J=252.4 Hz), 115.9 (d, 1=22.0 Hz), 114.2, 55.3. MS (EI): m/z (%) 280 (16), 157 (100). 135 (5). 123 (62). 114 (17). 95 (30). 75 (87). HRMS m/z: calcd for C$_{15}$H$_{11}$F$_3$O$_2$: 280.0711. Found: 280.0719.

2,2-Difluoro-2-(4-methoxyphenyl)-1-p-tolylethanone (3d)

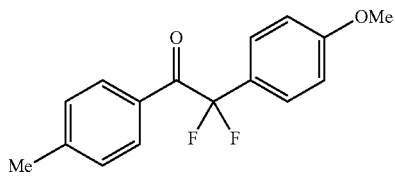 [SMILES: COc1ccc(C(F)(F)C(=O)c2ccc(C)cc2)cc1]

Prepared by coupling of 2,2-difluoro-1-(p-tolyl)ethan-1-one and 4-chloroanisole under conditions B [yield: 88%; 2 mol % complex 1 was used]. The title compound was isolated as a colorless oil after chromatography on silica with a Combiflash system (12 g column, 100:0→90:10 hexanes/EtOAc). $^1$H NMR (400 MHz, CDCl$_3$) δ 7.93 (d, J=8.1 Hz, 2H), 7.54 (d, J=8.8 Hz, 2H), 7.23 (d, J=8.1 Hz, 2H), 6.95 (d, J=8.7 Hz, 2H), 3.81 (s, 3H), 2.39 (s, 3H). $^{13}$C{$^1$H} NMR (101 MHz, CDCl$_3$) δ 188.7 (t, J=31.0 Hz), 161.4, 145.3, 130.4 (t, J=2.8 Hz), 129.6, 129.3, 127.2 (t, J=5.9 Hz), 125.3 (t, J=25.6 Hz), 117.0 (t, J=252.3 Hz), 114.1, 55.3, 21.7. $^{19}$F NMR (376 MHz, CDCl$_3$) δ −96.5 (s).

2,2-Difluoro-1,2-bis(4-methoxyphenyl)ethan-1-one (3e)

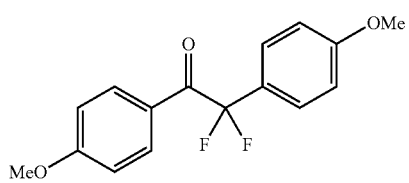 [SMILES: COc1ccc(C(=O)C(F)(F)c2ccc(OC)cc2)cc1]

This product was purified by silica gel chromatography with a CombiFlash system (12 g column, 100:0→90:10 hexanes/EtOAc). The title compound was isolated as a white solid (49.7 mg, 0.170 mmol, 85%). $^1$H NMR (400 MHz, CDCl$_3$) δ 8.03 (d, J=8.3 Hz, 2H), 7.53 (d, J=8.4 Hz, 2H), 6.95 (d, J=8.4 Hz, 2H), 6.91 (d, J=9.0 Hz, 2H), 3.85 (s, 3H), 3.82 (s, 3H). $^{13}$C NMR (101 MHz, CDCl$_3$) δ 187.5 (t, J=30.8 Hz), 164.2, 161.4, 132.8, (t, J=3.0 Hz), 127.1 (t, J=5.8 Hz), 125.5 (t, J=25.7 Hz), 125.0, 117.1 (t, J=252 Hz), 114.1, 113.9, 55.5, 55.3. $^{19}$F NMR (376 MHz, CDCl$_3$) δ −94.82. HRMS, m/z: calcd for C$_{16}$H$_{14}$F$_2$O$_2$: 276.0962. Found 276.0967.

α-Arylation of α,α-difluoroacetophenone with 2-(3-bromophenyl)-1,3-dioxolane on 2.0 mmol scale A 25 mL single Schlenk flask was charged with complex 1 (5.6 mg, 10 μmol, 0.5 mol %, weighed in air), K$_3$PO$_4$ (H$_2$O) (1.84 g, 8.00 mmol) and a magnetic stirring bar. The air in the flask was replaced with nitrogen by using vacuum-nitrogen sequence for three times. α,α-Difluoroacetophenone (625 mg, 530 μL, 4.00 mmol), 2-(3-bromophenyl)-1,3-dioxolane (458 mg, 303 μL, 2.00 mmol) and degassed toluene (6 mL) were added using an air-tight syringe. The mixture was heated in an oil bath preheated to 100° C. for 24 h and then cooled to room temperature. The reaction was quenched with H$_2$O (2 mL). The reaction mixture was extracted with diethyl ether (3×10 mL) and the combined ethereal fraction was dried over Na$_2$SO$_4$. All the volatile materials were removed under reduced pressure and the crude product was purified by flash chromatography on silica using ethyl acetate/hexanes (10% v/v) as eluent. The coupled product was isolated (543 mg, 1.78 mmol, 89%) as a viscous oil.

Nucleophilic addition of methyl Grignard reagent to α-aryl-α,α-difluoroacetophenone 2a: Synthesis of 1,1-Difluoro-2-phenyl-1-(4-(trifluoromethyl)phenyl)propan-2-ol

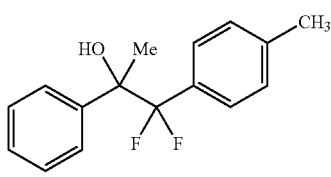 [SMILES: Cc1ccc(C(F)(F)C(C)(O)c2ccccc2)cc1]

This reaction was conducted in nitrogen atmosphere. To a solution of 2a (60.0 mg, 0.200 mmol) in anhydrous ether (2 mL) at −78° C. was added MeMgBr (0.1 mL, 3.0 M in ether) dropwise. After the addition was complete, the resulting mixture was stirred for 20 min at -78° C. and 30 min at room temperature, and then quenched with aqueous HCl (0.5 mL, 1.0 M). The mixture was extracted with ether (2×3 mL), and the combined ether extract was washed with a saturated aqueous NaHCO$_3$, and dried over Na$_2$SO$_4$. All the volatile materials were evaporated under vacuum, affording the title compound (54.1 mg, 0.171 mmol, 85%) as a yellow liquid. NMR (300 MHz, CDCl$_3$) δ 7.49 (d, J=8.2 Hz, 2H), 7.33-7.25 (m, 5H), 7.23 (d, J=8.3 Hz, 2H), 2.35 (s, 1H), 1.84 (t, J=1.3 Hz, 3H). $^{19}$F NMR (376 MHz, CDCl$_3$) δ −62.75 (s), −107.51 (dd, J=936, 248 Hz). $^{13}$C{$^1$H} NMR (101 MHz, CDCl$_3$) δ 139.1 (q, J=2.3 Hz), 136.7 (t, J=26.8 Hz), 130.9 (q, J=33.6 Hz), 127.3, 127.1, 126.9 (t, J=6.4 Hz), 125.8, 123.5 (q, J=3.7 Hz), 122.9 (q, J=273 Hz), 120.8 (t, J=252 Hz), 30.0. HRMS (ESI) m/z: calcd for C$_{16}$H$_{12}$F$_5$O: 315.0814 ([M−H]$^-$. Found 315.0812 ([M−H]$^-$).

Reduction of α-aryl-α,α-difluoroacetophenone with NaBH$_4$: Synthesis of 2,2-Difluoro-2-(naphthalen-2-yl)-1-phenylethan-1-ol

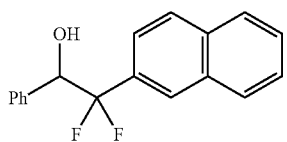 [SMILES: OC(c1ccccc1)C(F)(F)c1ccc2ccccc2c1]

A 4-mL crew-capped vial was charged with 2,2-Difluoro-2-(naphthalen-2-yl)-1-phenylethanone (56.5 mg, 0.200 mmol), NaBH$_4$ (30.3 mg, 0.800 mmol), ethanol (2 mL), and a magnetic stirring bar. The mixture was stirred at room temperature for 1 h and then carefully quenched with aqueous HCl (1M). The mixture was then extracted with ether (3×3 mL), and the combined organic fraction was dried over Na$_2$SO$_4$. The crude product was purified by flash chromatography on silica (20% ethyl acetate in hexanes), affording the title compound as a white solid (50.7 mg, 0.178 mmol, 89%). $^1$H NMR (600 MHz, CDCl$_3$) δ 7.83 (d, J=7.7 Hz, 1H), 7.79-7.72 (m, 2H), 7.70 (s, 1H), 7.49 (p, J=6.7 Hz, 2H), 7.41 (t, J=7.2 Hz, 1H), 7.35-7.24 (m, 5H), 5.24 (t, J=10.0 Hz, 1H), 2.76 (s, 1H). $^{19}$F NMR (376 MHz, CDCl$_3$) δ −105.5 (s). $^{13}$C {$^1$H} NMR (151 MHz, CDCl$_3$) δ 133.7 (t, J=25.7 Hz), 133.4, 133.2, 132.8, 130.0, 128.2, 127.9 (two peaks overlap), 127.6 (two peaks overlap), 127.4, 126.4, 126.3 (t, J=249 Hz), 126.1, 125.2, 121.2. HRMS (ESI) m/z: calcd for C$_{18}$H$_{13}$F$_2$O: 283.0940 ([M−H]$^-$). Found 283.0938 ([M−H]$^-$).

Example 2

Arylation of Trimethylsilyl Enol Ethers of α,α-Difluoroketones

Further to the above described palladium catalyzed direct arylation of α,α-difluoroketones we envisioned the application of α-aryl-β,β-difluoroenol silyl ethers as a coupling partner, in place of α,α-difluoroketones. We are pleased to find, that α-aryl-β,β-difluoroenol silyl ethers efficiently coupled with aryl bromides under conditions previously developed for direct coupling of α,α-difluoroketones; higher catalyst loading of 5 mol % is necessary, however. The procedure proved successful for coupling of a range of electronically distinct silyl enolates (eg. R=CF$_3$, OMe) with various aryl bromides. Interestingly, no Bu$_3$SnF is needed as an additive aiding transmetallation. Products of coupling of trimethylsilyl α-(4-methoxyphenyl)-β,β-difluoroenol ether undergo facile Baeyer-Villiger oxidation, opening a convenient route to α-aryl-α,α-difluoroacetates.

General Procedure for Acylation of Trimethylsilyl Enol Ethers of α,α-Difluoroketones In a nitrogen-filled glove box, a catalyst 1 (11.3 mg, 0.02 mmol), Cs$_2$CO$_3$ (260 mg, 0.8 mmol), aryl bromide (0.8 mmol), silyl enolate (0.4 mmol) and toluene (1 ml) were place in screw capped vial. The vessel was tightly closed, removed from glove box and the reaction was heated with magnetic stirring at 100° C. for 24h. After cooling to room temperature, the reaction mixture was diluted with Et$_2$O (2 ml), dodecane (50 μl) was added and the reaction was analyzed by GC (against dodecane as internal standard). Reaction mixture was transferred to 25 ml flask, diluted with CH$_2$Cl$_2$ (ca 15 ml) silica gel (~2 g) was added, the mixture was concentrated to dryness and purified by column chromatography (Combiflash, 12 g silica column, hexane-→hexane/EtOAc 8:2, flow rate 15 ml/min).

Reaction Scope
TABLE 3
Reaction of 2,2-difluoro-1-phenyl-ethanone with aryl bromides[a]
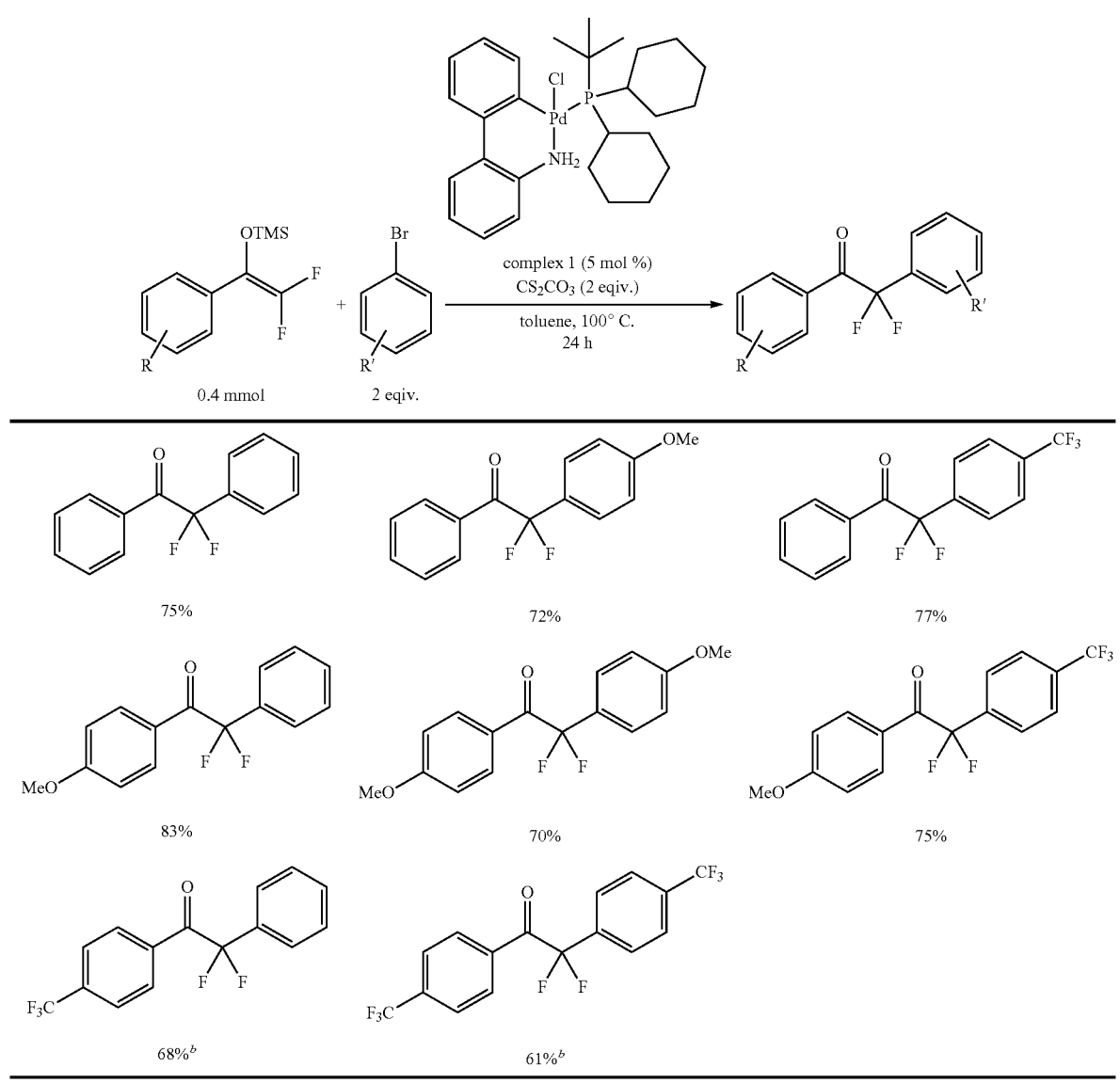
[a]Conditions: Silyl enol ether of α,α-difluoroketone (0.4 mmol), aryl bromide (0.8 mmol), Cs$_2$CO$_3$ (0.8 mmol), complex 1 (0.02 mmol, 5 mol %) in toluene (1 mol) at 100° C. for 24h;
[b]starting material was ~80% pure by NMR.
Example 3
Ketone Cleavage
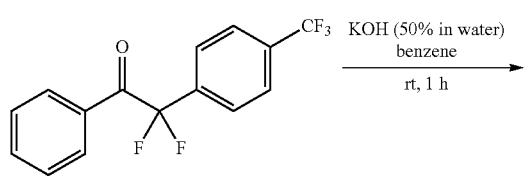
-continued
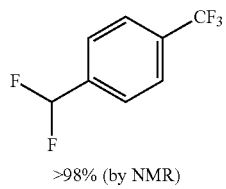
>98% (by NMR)
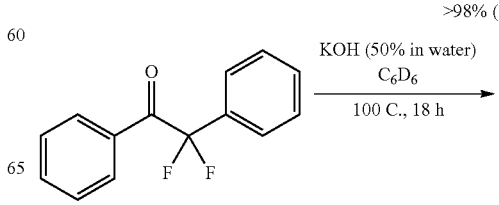

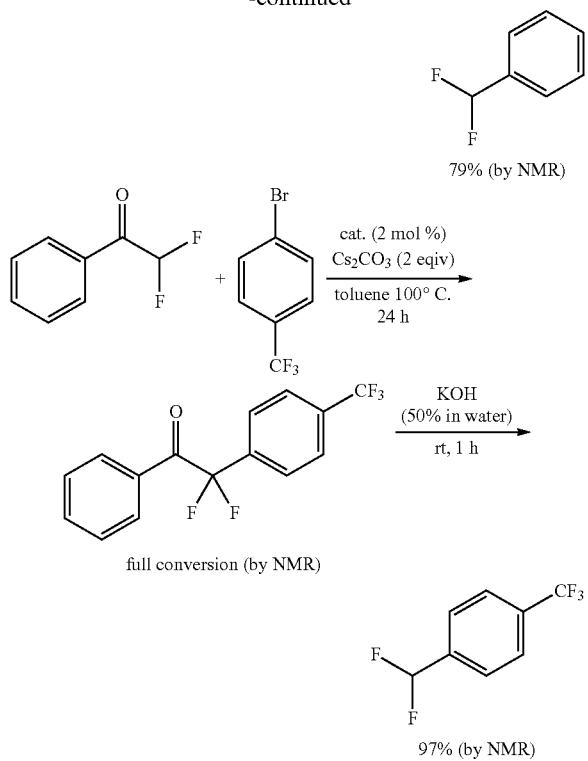

A. Formation of 4-difluoromethylquinoline during the coupling of 4-bromoquinoline with α,α-difluoroketones.

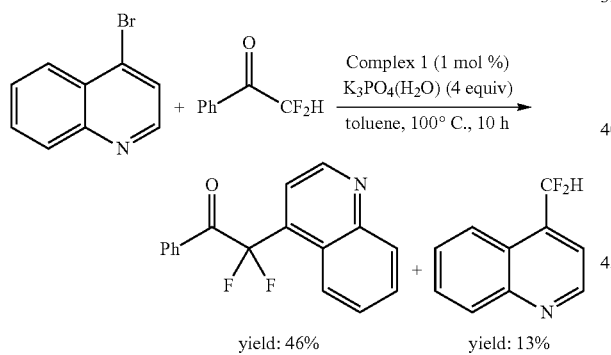

The investigation of the base-induced cleavage of the α-aryl-α,α-difluoroketone products to form difluoromethylarene was spurred by the observation of small but significant amounts of 4-difluoromethylquinoline (13%) from the coupling of α,α-difluoroacetophenone with 4-bromoquinoline (A, Scheme 2). We found that the analogous base-induced C—C cleavage of isolated α-phenyl-α,α-difluoroacetophenone (2e) occurred in the presence of KOH and H₂O in toluene at 100° C. (B, Scheme 2) to afford (difluoromethyl) benzene in quantitative yield in 2 h, as determined by $^{19}$F NMR spectroscopy.

Base-Induced C—C Cleavage of α-aryl-α,α-difluoroketones

Having demonstrated the α-arylation and the C—C bond cleavage as individual steps, we developed a one-pot procedure for the synthesis of difluoromethylarenes. The scope of aryl bromides and aryl chlorides that undergo the combination of α-arylation and the base-induced C—C bond cleavage is summarized in FIG. 2. In many cases, the resulting difluoromethylarenes are volatile, and the yields of these reactions were determined by $^{19}$F NMR spectroscopy with 1-bromo-4-fluorobenzene as an internal standard. Isolated yields were obtained for the reactions affording the difluoromethylarenes with high boiling points.

Figure 2:
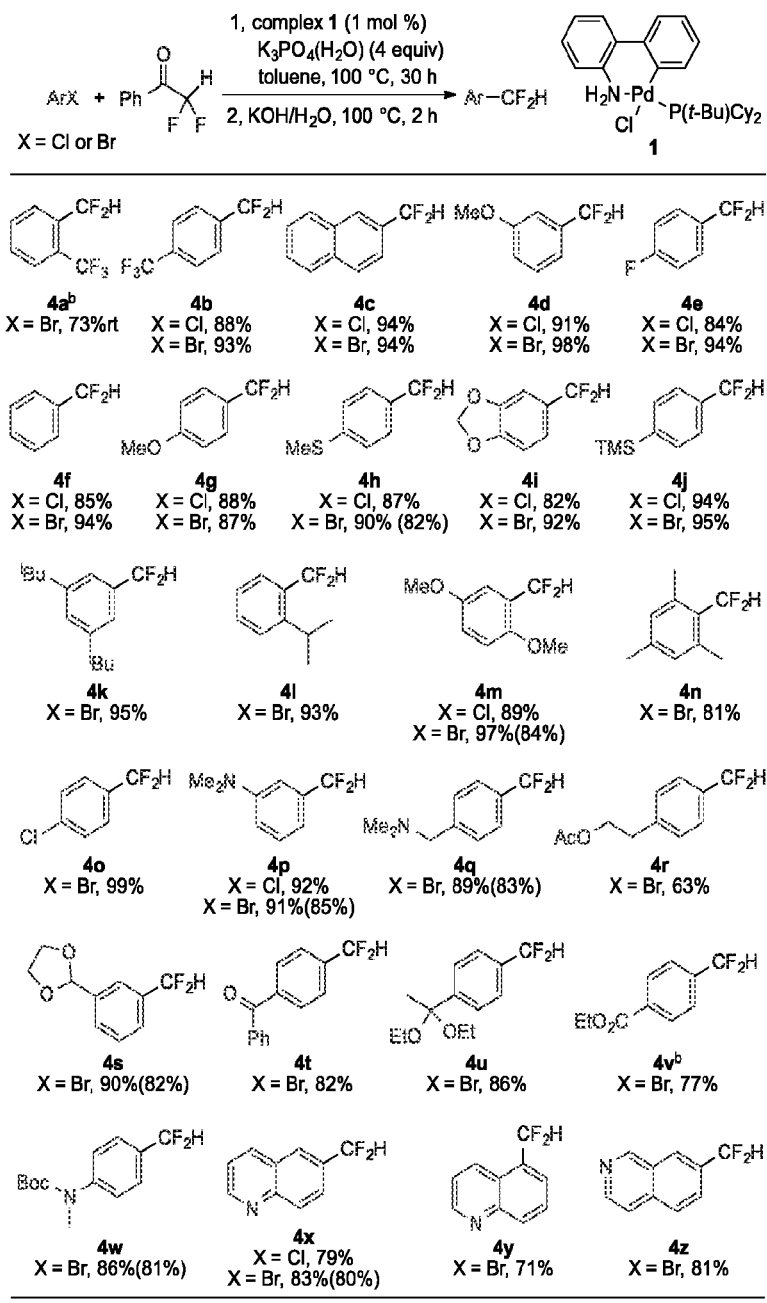
FIG. 2. One-pot synthesis of difluoromethylarenes. Conditions: Step 1: aryl bromide or aryl chloride (0.200 mmol), α,α-difluoroacetophenone (0.400 mmol), $K_3PO_4(H_2O)$ (0.800 mmol), complex 1 (2 μmol), toluene (1 mL), 100° C. for aryl bromide and 110° C. for aryl chloride, 30 h. Step 2: KOH (100 mg), $H_2O$ (50 μL), 100° C., 2 h. Yields are determined by $^{19}F$ NMR spectroscopy with 1-bromo-4-fluorobenzene as internal standard; Isolated yields are shown in parentheses for products with high boiling points. [b]Step 2 was conducted at room temperature.

The scope of aryl bromides and aryl chlorides that undergo this transformation mirrors the scope of aryl bromides and aryl chlorides that undergo Pd-catalyzed α-arylation of α,α-difluoroacetophenone described in FIG. 2. In general, a wide range of electronically varied aryl bromides and aryl chlorides underwent the reaction sequence to afford the corresponding difluoromethylarenes in high yields. Reactions of aryl chlorides afforded the desired products in yields comparable to those of the reactions of aryl bromides (4b-4j, 4m, 4p, and 4x). Like the single-step coupling reaction, the sequential reactions tolerate a range of functionalities, including ether (4d, 4g, and 4i), thioether (4h), ester (4r and 4v), non-enolizable ketone (4t), and carbamate (4w) moieties. Reactions of 1-bromo-4-chlorobenzene occurred selectively at the bromide (4o), and aryl bromides containing N,N-dimethylamino (4p), dimethylaminomethyl (4q), protected alcohol (4r), protected aldehyde (4s), and protected enolizable ketone (4u) functionality reacted to form the corresponding difluoromethylarenes in high yields. Brominated nitrogen-containing heterocycles, such as quinolines (4x and 4y) and isoquinoline (4z), also gave the difluoromethyl heteroarenes in good yields.

Example 4

Baeyer-Villiger Oxidation

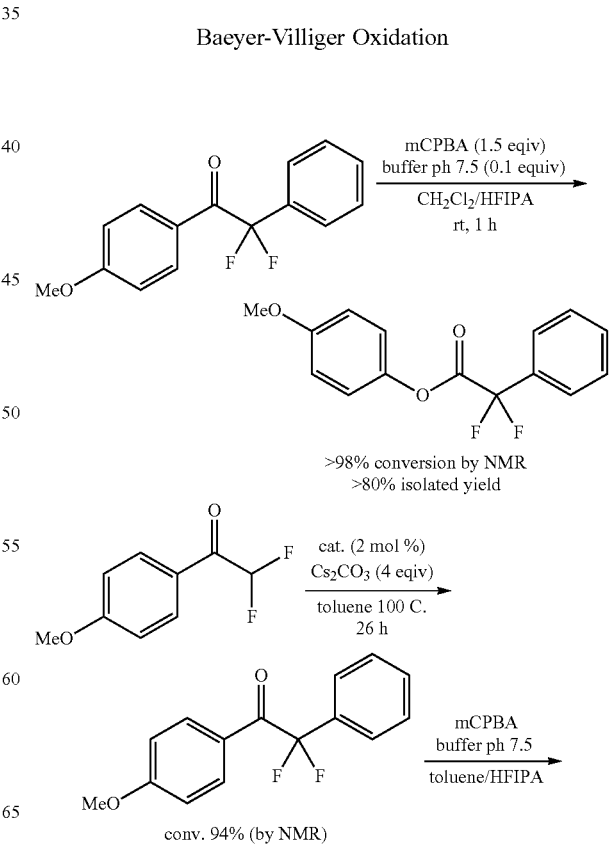

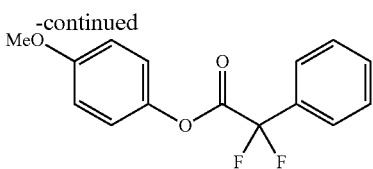

One pot procedure. After coupling cesium carbonate was filtered off and reagents (mCPBA, buffer) and co-solvent (IFIPA) were added.

| Entry | condition | conversion (by $^{19}$F NMR) |
|---|---|---|
| 1 | mCPBA (1.25 eqiv), buffer (0.1 quiv), rt, 1 h | 9% |
| 2 | Entry 1 + mCPBA (1.25 eqiv), buffer (0.1 quiv), rt, 16 h | 41% |
| 3 | Entry 2 + mCPBA (1.25 eqiv), 40° C. 4 h | 49% |

Related literature for the Baeyer-Villiger oxidation: Kobayashi, S.; Tanaka, H.; Amii, H.; Uneyama, K. *Tetrahedron* 2003, 59 1547-1552.

Example 5

Catalyst Preparation

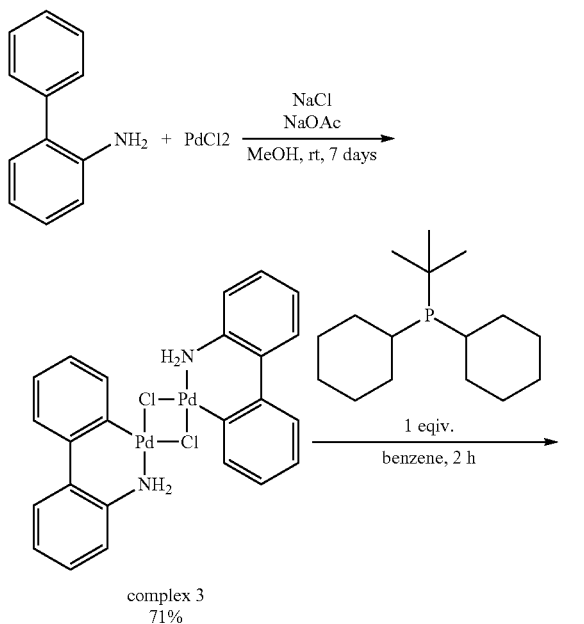

Palladium precursor 3 was prepared in 71% yield following the reported procedure: Albert, J; Granell, J.; Zafrilla, J.; Font-Bardia, M.; Solans, X. *J. Organomet. Chem.* 2005, 690 422.

Preparation of Complex 1.

In a glove box a mixture of palladium precursor 3 (930.3 mg, 1.50 mmol) and ten-butyldicyclohexylphosphine (763.0 mg, 3.00 mmol) in benzene (60 ml) was stirred at r.t. for 1 h (after ca. 10 min reaction mixture turned homogenous). Reaction mixture was removed from the glovebox. The solution was filtrated through the pad of Celite and concentrated to volume of ca. 4 ml. Pentane (60 ml) was added and the mixture was left to crystallize overnight. Solid was collected by filtration, washed with pentane (3×5 ml) and dried under vacuum giving complex 1 (1.575 g, 2.79 mmol, 93%)$^1$H NMR (400 MHz, $C_6D_6$) δ 7.67 (d, J=6.1 Hz, 1H), 7.41 (d, J=7.3 Hz, 1H), 7.34-7.27 (m, 1H), 7.20-7.12 (m, 2H), 7.02 (t, J=7.4 Hz, 1H), 6.97 (t, J=7.4 Hz, 1H), 6.76 (d, J=7.5 Hz, 1H), 4.55 (brs, 1H), 3.56 (brs, 1H), 2.60 (brs, 1H), 2.52-2.28 (m, 2H), 2.28-1.99 (m, 2H), 1.32 (d, J=13.1 Hz, 9H), 1.91-0.73 (m, 17H); $^{31}$P NMR (162 MHz, $C_6D_6$) δ 56.2 (s); Anal. Calcd for $C_{28}H_{41}ClNPPd$: C, 59.58; H, 7.32; N, 2.48. Found: C, 59.66; H, 7.46; N, 2.41.

Example 6

Procedure for the One-Pot Synthesis of Difluoromethylarenes

In a drybox, a 4-mL screw-capped vial was charged with complex 1 (1.1 mg, 2.0 μmol), aryl bromide (0.200 mmol), α,α-difluoroacetophenone (62.5 mg, 0.400 mmol), $K_3PO_4$ ($H_2O$) (184 mg, 0.800 mmol), toluene (1 mL), and a magnetic stirring bar. The vial was sealed with a cap containing a PTFE septum and removed from the drybox. The reaction mixture was stirred at 100° C. for 30 h and then cooled to room temperature. To the mixture, was added KOH (100 mg) and $H_2O$ (50 mg), and the resulting suspension was stirred at 100° C. for 2 h. After the mixture was cooled to room temperature, 1-bromo-4-fluorobenzene (0.400 mmol) was added as an internal standard using an air-tight syringe to determine the yields of the resulting difluoromethylarenes by $^{19}$F NMR spectroscopic analysis. To isolate the difluoromethylarenes having high boiling points, the mixture was diluted with $H_2O$ (1 mL) and extracted with $Et_2O$ (3×3 mL). To the ethereal extract, silica (4 mL) was added and all the volatile materials were evaporated under reduced pressure. The crude product was purified with a CombiFlash system with 1-20% ether in pentane as eluent. The conditions for chromatography and data for characterization of the products are given below.

(4-(difluoromethyl)phenyl)(methyl)sulfane (4h)

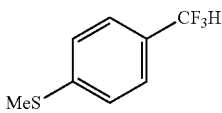

The NMR yield for this reaction was 90% as determined by $^{19}$F NMR spectroscopy with 1-bromo-4-fluorobenzene as an internal standard. The crude product was purified by silica gel chromatography with a CombiFlash system (4 g column, 100:0→90:10 hexanes/EtOAc). The title compound was isolated as colorless oil in 82% yield. $^1$H NMR (400 MHz, CDCl$_3$) δ 7.42 (d, J=8.3 Hz, 2H), 7.30 (d, J=8.4 Hz, 2H), 6.62 (t, J=56.6 Hz, 1H), 2.51 (s, 3H). $^{13}$C{$^1$H} NMR (101 MHz, CDCl$_3$) δ 142.2, 130.8 (t, J=22.9 Hz), 126.0 (t, J=5.9 Hz), 125.9, 114.6 (t, J=238 Hz), 15.2. $^{19}$F NMR (376 MHz, CDCl$_3$) δ −109.28 (d, J=56.6 Hz).

1-(difluoromethyl)-2-isopropylbenzene (4l)

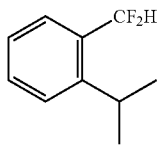

The NMR yield for this reaction was 93% as determined by $^{19}$F NMR spectroscopy with 1-bromo-4-fluorobenzene as an internal standard. This product was prepared by Haller-Bauer reaction of 2k in NMP (1-methyl-2-pyrolidinone) in the presence of KOH and H$_2$O at 100° C. After the reaction, NMP was removed by diluting the mixture with ether and washing the mixture with H$_2$O. The crude product was purified by silica gel chromatography with a CombiFlash system (4 g column, pentane). $^1$H NMR (400 MHz, CDCl$_3$) δ 7.52 (d, J=7.8 Hz, 1H), 7.50-7.37 (m, 2H), 7.33-7.23 (m, 1H), 6.87 (t, J=55.5 Hz, 1H), 3.28 (hept, J=6.7 Hz, 1H), 1.29 (d, J=6.8 Hz, 7H). $^{13}$C NMR (101 MHz, CDCl$_3$) δ 147.3 (t, J=4.3 Hz), 130.9 (t, J=1.7 Hz), 130.8 (t, J=20.8 Hz), 126.0, 125.9, 125.7 (t, J=7.7 Hz), 114.0 (t, J=238 Hz), 28.6, 24.0.

2-(difluoromethyl)-1,4-dimethoxybenzene (4m)

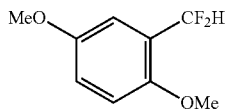

The NMR yield for this reaction was 97% as determined by $^{19}$F NMR spectroscopy with 1-bromo-4-fluorobenzene as an internal standard. The crude product was purified by silica gel chromatography with a CombiFlash system (4 g column, 100:0→90:10 hexanes/EtOAc). The title compound was isolated as slightly yellow oil in 84% yield. $^1$H NMR (400 MHz, CDCl$_3$) δ 7.13 (d, J=3.0 Hz, 1H), 7.00-6.95 (m, 1H), 6.94 (t, J=55.7 Hz), 6.92-6.83 (m, 1H), 3.83 (s, 3H), 3.81 (s, 3H). $^{13}$C{$^1$H} NMR (101 MHz, CDCl$_3$) δ 153.5, 151.4 (t, J=6.1 Hz), 123.2 (t, J=22.2 Hz), 117.3 (t, J=2.1 Hz), 112.3, 111.3 (t, J=236 Hz), 111.3 (t, J=6.0 Hz), 56.2, 55.8. $^{19}$F NMR (376 MHz, CDCl$_3$) δ −114.58 (d, J=55.7 Hz).

2-(3-(difluoromethyl)phenyl)-1,3-dioxolane (4s)

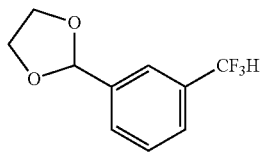

The NMR yield for this reaction was 90% as determined by $^{19}$F NMR spectroscopy with 1-bromo-4-fluorobenzene as an internal standard. The crude product was purified by silica gel chromatography with a CombiFlash system (4 g column, 100:0→90:10 hexanes/EtOAc). The title compound was isolated as slightly yellow oil in 82% yield. $^1$H NMR (400 MHz, CDCl$_3$) δ 7.73-7.43 (m, 4H), 6.68 (t, J=56.4 Hz, 1H), 5.86 (s, 1H), 4.23-4.02 (m, 4H). $^{13}$C{$^1$H} NMR (101 MHz, CDCl$_3$) δ 138.8, 134.5 (t, J=22.6 Hz), 128.9, 128.8, 126.3 (t, J=6.0 Hz), 123.8 (t, J=6.1 Hz), 116.9 (t, J=239 Hz), 103.1, 65.4. $^{19}$F NMR (376 MHz, CDCl$_3$) δ −110.02 (d, J=56.4 Hz).

tert-Butyl (4-(difluoromethyl)phenyl)(methyl)carbamate (4w)

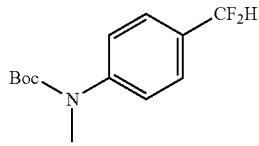 [SMILES: CN(C(=O)OC(C)(C)C)c1ccc(C(F)F)cc1]

The NMR yield for this reaction was 86% as determined by $^{19}$F NMR spectroscopy with 1-bromo-4-fluorobenzene as an internal standard. The crude product was purified by silica gel chromatography with a CombiFlash system (4 g column, 100:0→85:15 hexanes/EtOAc). The title compound was isolated as colorless oil in 81% yield. $^1$H NMR (600 MHz, CDCl$_3$) δ 7.46 (d, J=8.3 Hz, 2H), 7.34 (d, J=8.3 Hz, 2H), 6.62 (t, J=56.5 Hz, 1H), 3.28 (s, 3H), 1.46 (s, 9H). $^{13}$C NMR (151 MHz, CDCl$_3$) δ 154.4, 145.9, 130.9 (t, J=22.8 Hz), 125.9 (t, J=6.0 Hz), 125.2, 114.5 (t, J=238 Hz), 80.8, 37.0, 28.3. HR-MS (ESI) exact mass calcd for C$_{13}$H$_{17}$F$_2$NO$_2$: m/z 257.1227. Found: 257.1225.

6-(Difluoromethyl)quinoline (4x)

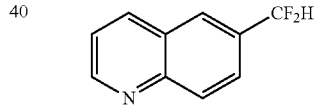

The NMR yield for this reaction with 6-bromoquinoline was 83% as determined by $^{19}$F NMR spectroscopy with 1-bromo-4-fluorobenzene as an internal standard. The crude product was purified by silica gel chromatography with a CombiFlash system (4 g column, 100:0→85:15 pentane/diethyl ether). The title compound was isolated as colorless oil in 80% yield. $^1$H NMR (400 MHz, CDCl$_3$) δ 8.97 (dd, J=4.2, 1.6 Hz, 1H), 8.22-8.15 (m, 2H), 7.95 (d, J=1.4 Hz, 1H), 7.81 (dd, J=8.8, 1.8 Hz, 1H), 7.45 (dd, J=8.3, 4.3 Hz, 1H), 6.81 (t, J=56.2 Hz, 1H). $^{13}$C {1H} NMR (101 MHz, CDCl$_3$) δ 151.8, 148.9, 136.6, 132.0 (t, J=22.6 Hz), 130.5, 127.5, 125.7, 125.3 (dd, J=12.1, 2.4 Hz), 121.9, 114.4 (t, J=239.2 Hz). $^{19}$F NMR (376 MHz, CDCl$_3$) δ −111.0 (d, J=56.2 Hz). HRMS, m/z: calc'd for C$_{10}$H$_7$F$_2$N: 179.0547. Found 179.0540.

Example 7

Procedure for Pd-Catalyzed Arylation of α,α-Difluoro-α-Trimethylsilylamide

In a drybox, a 4-mL screw-capped vial was charged with complex 1 (3.2 mg, 6.0 μmol), aryl bromide (0.200 mmol), α,α-difluoro-α-trimethylsilylamide (0.400 mmol), KF (34.9 mg, 0.600 mmol), toluene (0.2 mL), 1,4-dioxane (0.8 mL) and a magnetic stirring bar. The vial was sealed with a cap containing a PTFE septum and removed from the drybox. The reaction mixture was stirred at 100° C. for 24 h and then cooled to room temperature. The mixture was quenched with $H_2O$ (0.5 mL) and extracted with $Et_2O$ (3×3 mL). To the ethereal extract, silica (4 mL) was added, and all the volatile materials were evaporated under reduced pressure. The crude product was purified with a CombiFlash system with 5-70% ethyl acetate in hexanes as eluent.

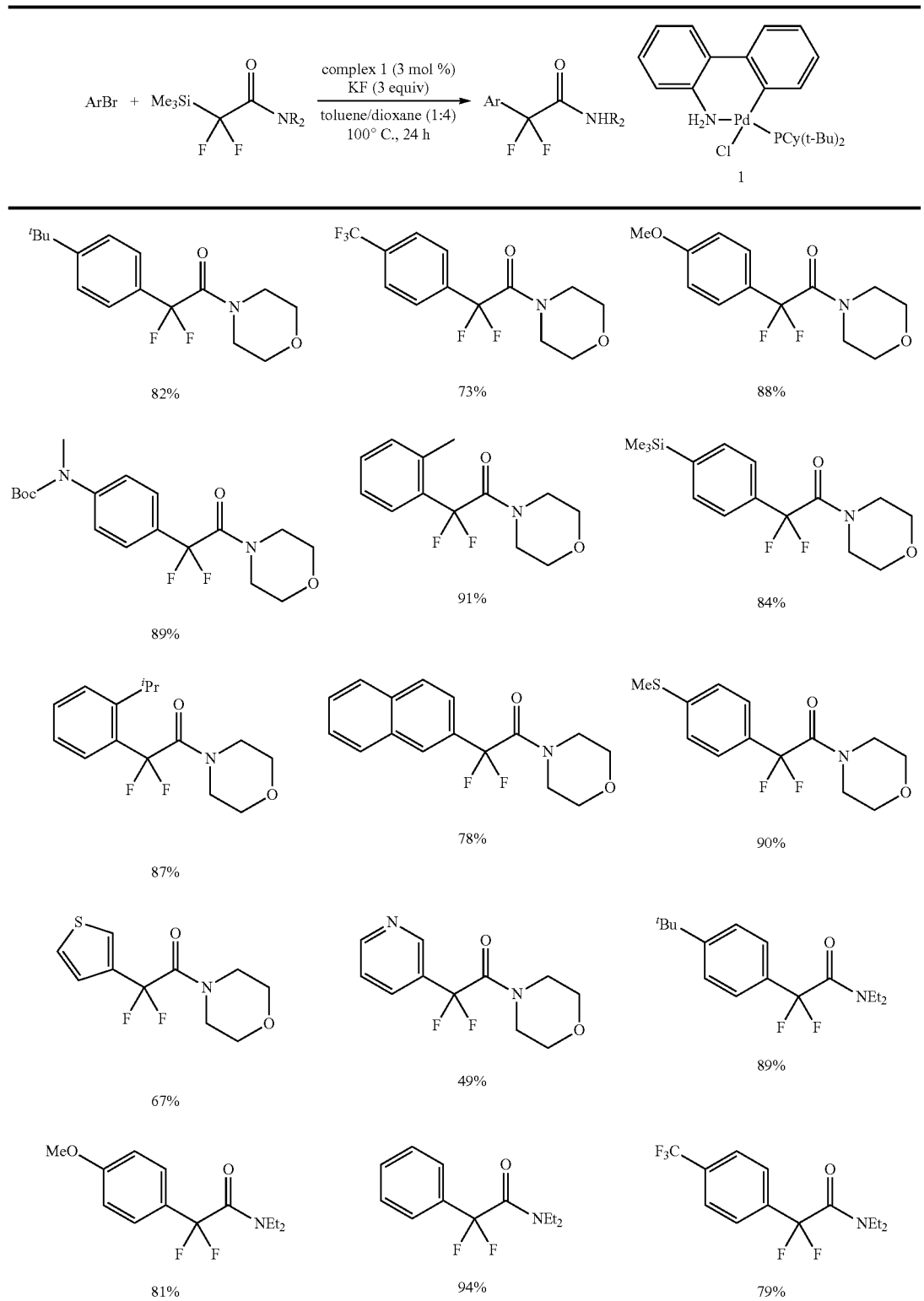

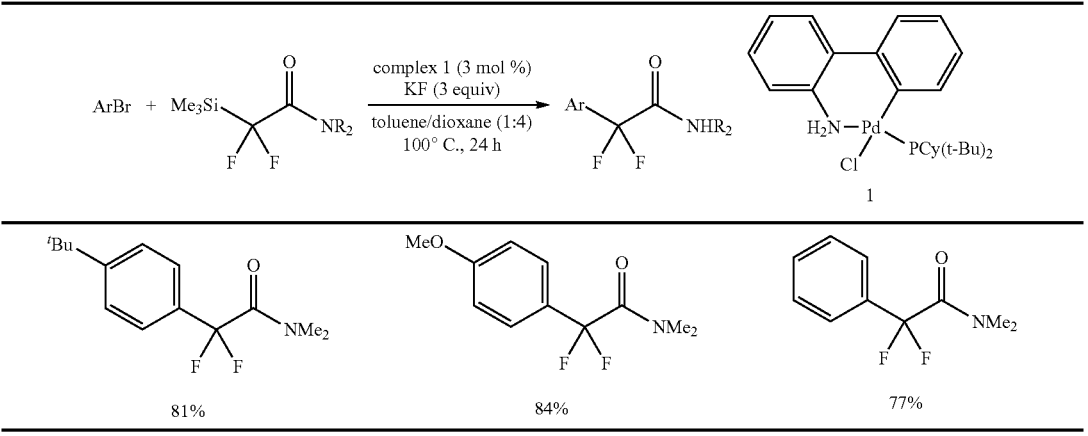

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising:
   (i) a precursor compound having the formula $R^P$—$X^L$, wherein $R^P$ is a member selected from substituted or unsubstituted aryl, substituted or unsubstituted heteroaryl, and substituted or unsubstituted vinyl; and $X^L$ is a member selected from Cl, Br, and I;
   (ii) an α,α-difluoro synthon having a formula selected from:

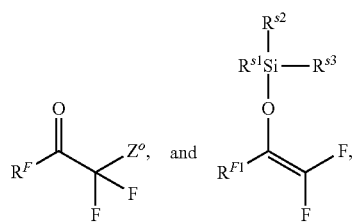

wherein $R^F$ is a member selected from substituted or unsubstituted aryl, and substituted or unsubstituted heteroaryl, substituted or unsubstituted alkyl substituted or unsubstituted heteroalkyl $OR^{z1}$ and $NR^{z2}R^{z3}$,
   $R^{F1}$ is a member selected from substituted or unsubstituted aryl, and substituted or unsubstituted heteroaryl,
   wherein $R^{z1}$ is a member selected from substituted or unsubstituted alkyl, substituted or unsubstituted heteoalkyl, substituted or unsubstituted aryl, substituted or unsubstituted heteroaryl and acyl; and
   $R^{z2}$ and $R^{z3}$ are members independently selected from H, substituted or unsubstituted alkyl, substituted or unsubstituted heteroalkyl, substituted or unsubstituted aryl, substituted or unsubstituted heteroaryl, acyl and sulfonyl, and $R^{z2}$ and $R^{z3}$, together with the nitrogen to which they are attached, are optionally joined to form a 4-8 membered ring, which is a substituted or unsubstituted heterocycloalkyl or heteroaryl ring system;
   $Z^o$ is selected from H or $Si(R^{30})_3$, in which each $R^{30}$ is independently selected from H, substituted or unsubstituted alkyl, substituted or unsubstituted heteroalkyl substituted or unsubstituted aryl, substituted or unsubstituted heteroaryl substituted or unsubstituted alkoxy, halogen, amino, and two or more of $R^{30}$, together with the Si atom to which they are attached are optionally joined to form a 4-8-membered ring,
   wherein, $Z^o$ is $Si(R^{30})_3$, the silicon enolate can have Si bound to a member selected from the alpha carbon, oxygen or a combination thereof; and
   $R^{s1}$, $R^{s2}$, and $R^{s3}$ are independently selected from H, substituted or unsubstituted alkyl, substituted or unsubstituted cycloalkyl, substituted or unubstituted heteroalkyl, substituted or unsubstituted heterocycloalkyl, substituted or unsubstituted aryl, and substituted or unsubstituted heteroaryl;
   (iii) a complex comprising palladium and a ligand, wherein said ligand comprises a trialkylphosphine moiety, wherein, when $R^F$ is substituted or unsubstituted aryl at least one of the alkyl groups of said trialkylphosphine is not a tertiary alkyl group; and
   (iv) a base.

2. The composition according to claim 1, wherein said complex is present in said composition in an amount of less than 10 mol % relative to said α,α-difluoromethyl synthon.

3. The composition according to claim 1, wherein said complex is present in said composition in an amount of less than 10 mol % relative to said silyl enol ether.

4. The composition according to claim 1, wherein said composition does not contain $Bu_3SnF$.

5. The composition according to claim 1, wherein said composition does not contain an organotin reagent.

6. The composition according to claim 1, wherein $R^{s1}$, $R^{s2}$, and $R^{s3}$ are independently selected from unsubstituted $C_1$, $C_2$, $C_3$, $C_4$, $C_5$ and $C_6$ alkyl.

7. The composition according to claim 6, wherein one or more of $R^{s1}$, $R^{s2}$, and $R^{s3}$ are methyl.

8. The composition according to claim 1, further comprising a solvent.

9. The composition according to claim 1, wherein said complex has the formula:

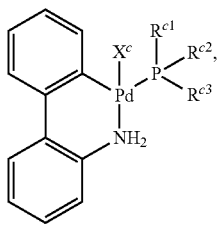

wherein
X$^c$ is a halogen or sufonate; and
R$^{c1}$, R$^{c2}$, and R$^{c3}$ are independently selected from substituted or unsubstituted branched hydrocarbon and substituted or unsubstituted carbocycle.

10. The composition according to claim 1, wherein said precursor compound has the formula:

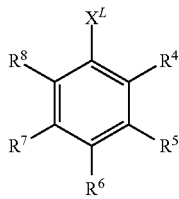

wherein
R$^4$, R$^5$, R$^6$, R$^7$, and R$^8$ are independently members selected from H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^9$R$^{10}$, —NR$^9$R$^{10}$, —OR$^9$, —S(O)$_2$R$^9$, —C(O)R$^9$, —COOR$^9$, —CONR$^9$R$^{10}$, —S(O)$_2$OR$^9$, —OC(O)R$^9$, —C(O)NR$^9$R$^{10}$, —NR$^9$C(O)R$^{10}$, —NR$^9$SO$_2$R$^{10}$ and —NO$_2$, wherein two or more of R$^4$, R$^5$, R$^6$, R$^7$ and R$^8$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl,
wherein
R$^9$ and R$^{10}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and R$^9$ and R$^{10}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl; and
X$^L$ is a member selected from Cl, Br, and I.

11. The composition according to claim 1, wherein R$^P$ is a member selected from substituted or unsubstituted five-membered heterorayl and substituted or unsubstituted six-membered heteroaryl.

12. The composition according to claim 1, wherein said precursor compound has the formula:

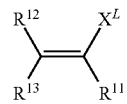

wherein
R$^{11}$, R$^{12}$, and R$^{13}$ are independently members selected from H, substituted or unsubstituted alkyl, substituted or unsubstituted heteroalkyl, substituted or unsubstituted aryl, substituted or unsubstituted heteroaryl, halogen, CN, CF$_3$, acyl, —SO$_2$NR$^9$R$^{10}$, —NR$^9$R$^{10}$, —OR$^9$, —S(O)$_2$R$^9$, —C(O)R$^9$, —COOR$^9$, —CONR$^9$R$^{10}$, —S(O)$_2$OR$^9$, —OC(O)R$^9$, —C(O)NR$^9$R$^{10}$, —NR$^9$C(O)R$^{10}$, —NR$^9$SO$_2$R$^{10}$ and —NO$_2$, wherein two or more of R$^{11}$, R$^{12}$, and R$^{13}$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl,
wherein
R$^9$ and R$^{10}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and R$^9$ and R$^{10}$, together with the atoms to which they are bonded, are optionally joined to form a 5- to 7-membered ring.

13. The composition according to claim 1, wherein said complex is generated in situ.

14. A method of forming a compound having the formula:

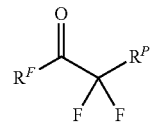

wherein
R$^F$ is a member selected from substituted or unsubstituted aryl, and substituted or unsubstituted heteroaryl, substituted or unsubstituted alkyl, substituted or unsubstituted heteroalkyl, OR$^{z1}$ and NR$^{z2}$R$^{z3}$,
such that when R$^F$ is substituted or unsubstituted alkyl or substituted or unsubstituted heteroalkyl, this group does not include enolizable hydrogens a to the carbonyl moiety,
wherein
R$^{z1}$ is selected from substituted or unsubstituted alkyl, substituted or unsubstituted heteroalkyl, substituted or unsubstituted aryl, substituted or unsubstituted heteroaryl, and acyl, and
R$^{z2}$ and R$^{z3}$ are independently selected from H, substituted or unsubstituted alkyl, substituted or unsubstituted heteroalkyl, substituted or unsubstituted aryl, substituted or unsubstituted heteroaryl, acyl and sulfonyl, and
R$^{z2}$ and R$^{z3}$, together with the nitrogen to which they are attached, are optionally joined to form a 4-8 membered ring, which is a substituted or unsubstituted heterocloalkyl or heteroaryl ring system; and
R$^P$ is a member selected from substituted or unsubstituted aryl, substituted or unsubstituted heteroaryl, and substituted or unsubstituted vinyl;

said method comprising:
(a) forming a composition according to claim 1; and
(b) incubating said composition under conditions appropriate to form said compound by coupling the precursor compound with the α,α-difluoromethyl synthon.

15. A method of forming a difluoromethyl compound having the formula:

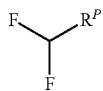

wherein R$^P$ is a member selected from substituted or unsubstituted aryl, substituted or unsubstituted heteroaryl, and substituted or unsubstituted vinyl;
said method comprising:
(a) forming a composition according to claim 1;
(b) incubating said composition under conditions appropriate to form a compound having the formula:

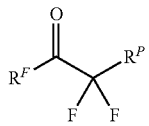

wherein R$^F$ is a member selected from substituted or unsubstituted aryl, and substituted or unsubstituted heteroaryl; and
(c) cleaving the compound formed in step (b) with base to form said difluoromethyl compound.

16. The method according to claim 15, wherein the base in step (c) is aqueous KOH.

17. The method according to claim 15, wherein step (c) is performed in situ.

18. A method of forming a difluoroacetate having the formula:

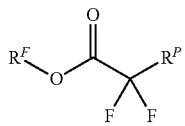

wherein R$^F$ is a member selected from substituted or unsubstituted aryl, and substituted or unsubstituted heteroaryl; and R$^P$ is a member selected from substituted or unsubstituted aryl, substituted or unsubstituted heteroaryl, and substituted or unsubstituted vinyl;

said method comprising:
(a) forming a composition according to claim 1;
(b) incubating said composition under conditions appropriate to form a compound having the formula

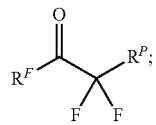

and
(c) reacting the compound formed in step (b) with an oxidizing agent to form said difluoroacetate.

19. The method according to claim 18, wherein said oxidizing agent is mCPBA.

20. The method according to claim 18, further comprising the step of filtering the composition between steps (b) and (c).

21. A palladium complex having a formula selected from:

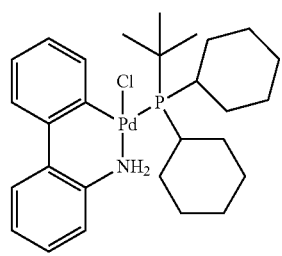

,

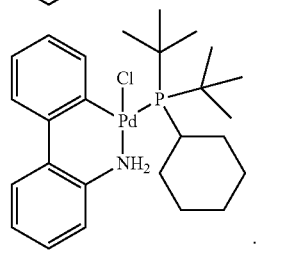

.

22. The composition according to claim 9, wherein X$^c$ is methanesulfonate.

23. The composition according to claim 9, wherein R$^{c1}$, R$^{c2}$, and R$^{c3}$ are independently selected from substituted or unsubstituted branched tert-butyl and substituted or unsubstituted cyclohexyl.

* * * * *